United States Patent
Mertz et al.

(10) Patent No.: US 10,123,995 B2
(45) Date of Patent: Nov. 13, 2018

(54) FACTOR XIA INHIBITORS

(71) Applicant: MERCK SHARP & DOHME CORP., Rahway, NJ (US)

(72) Inventors: Eric Mertz, Christiansburg, VA (US); Weiguo Liu, Princeton, NJ (US); Scott D. Edmondson, Clark, NJ (US); Amjad Ali, Freehold, NJ (US); Ying-Duo Gao, Holmdel, NJ (US); Santhosh F. Neelamkavil, Edison, NJ (US); Sung-Sau So, Verona, NJ (US); Remond Moningka, Jersey City, NJ (US); Wanying Sun, Edison, NJ (US); Alan Hruza, Hackettstown, NJ (US); Linda L. Brockunier, Orange, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/542,948

(22) PCT Filed: Jan. 15, 2016

(86) PCT No.: PCT/US2016/013507
§ 371 (c)(1),
(2) Date: Jul. 12, 2017

(87) PCT Pub. No.: WO2016/118403
PCT Pub. Date: Jul. 28, 2016

(65) Prior Publication Data
US 2018/0000795 A1    Jan. 4, 2018

Related U.S. Application Data

(60) Provisional application No. 62/105,385, filed on Jan. 20, 2015.

(51) Int. Cl.
| | |
|---|---|
| *A61K 31/435* | (2006.01) |
| *A61K 31/4375* | (2006.01) |
| *A61K 31/195* | (2006.01) |
| *A61P 7/02* | (2006.01) |
| *A61P 7/04* | (2006.01) |
| *C07D 221/18* | (2006.01) |
| *C07D 221/04* | (2006.01) |
| *C07D 401/10* | (2006.01) |

(52) U.S. Cl.
CPC .......... *A61K 31/435* (2013.01); *A61K 31/195* (2013.01); *A61K 31/4375* (2013.01); *A61P 7/02* (2018.01); *A61P 7/04* (2018.01); *C07D 221/04* (2013.01); *C07D 221/18* (2013.01); *C07D 401/10* (2013.01)

(58) Field of Classification Search
CPC ................................ C07D 487/02; A61P 7/02
See application file for complete search history.

(56) References Cited

U.S. PATENT DOCUMENTS

| | | | |
|---|---|---|---|
| 2009/0181983 A1* | 7/2009 | Corte | C07D 213/40 514/256 |
| 2010/0173899 A1 | 7/2010 | Pinto et al. | |
| 2011/0028481 A1 | 2/2011 | Berger et al. | |

FOREIGN PATENT DOCUMENTS

| | | | | |
|---|---|---|---|---|
| WO | 2007109459 A3 | 1/2008 | | |
| WO | 2012101011 A2 | 8/2012 | | |
| WO | 2013028474 A1 | 2/2013 | | |
| WO | 2014034898 A1 | 3/2014 | | |
| WO | 2014081618 A1 | 5/2014 | | |
| WO | WO 2014/081618 | * 5/2014 | ........... | A61K 31/165 |
| WO | 2015183709 A1 | 12/2015 | | |
| WO | 2016015593 A1 | 2/2016 | | |
| WO | 2016018701 A1 | 2/2016 | | |
| WO | 2016018702 A1 | 2/2016 | | |

OTHER PUBLICATIONS

International Search Report and Written Opinion for PCT/US2016/013507, dated Mar. 31, 2016, 9 pages.
Supplementary European Search Report for 16740526.5 dated May 28, 2018, 5 pages.

* cited by examiner

*Primary Examiner* — Erich A Leeser
(74) *Attorney, Agent, or Firm* — Nicole M. Beeler; John C. Todari

(57) ABSTRACT

The present invention provides a compound of Formula (I) and pharmaceutical compositions comprising one or more said compounds, and methods for using said compounds for treating or preventing thromboses, embolisms, hypercoagulability or fibrotic changes. The compounds are selective Factor XIa inhibitors or dual inhibitors of Factor XIa and plasma kallikrein.

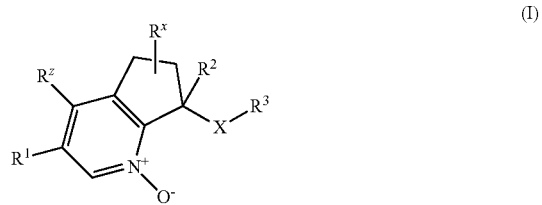

(I)

14 Claims, No Drawings

FACTOR XIA INHIBITORS

CROSS REFERENCE TO RELATED APPLICATIONS

This application is a U.S. National Phase application under 35 U.S.C. § 371 of PCT Application No. PCT/US2016/013507 filed Jan. 15, 2016, which claims priority from U.S. Provisional Application Ser. No. 62/105,385 filed Jan. 20, 2015.

BACKGROUND OF THE INVENTION

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commence after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. The activation of factor XIa is a central point of intersection between the two pathways of activation of clotting. Factor XIa has an important role in blood clotting.

Coagulation is initiated when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor 25 XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., Blood, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact ActivationPathway", Hemostasis and Thrombosis, pp. 103-122, Lippincott Williams & Wilkins (2001); Schmaier, A. H., "Contact Activation", Thrombosis and Hemorrhage, pp. 105-128 (1998)). The biological relevance of the contact activation system for thromboembolic 5 diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., J Exp. Med., 202:271-281 (2005); Kleinschmitz et al., J Exp. Med., 203:513-518 (2006)). The fact that factor XI is downstream from factor XIIa, combined with the identical phenotype of the XII and XI deficient mice suggest that the contact activation system could play a major role in factor XI activation in vivo. Plasma kallikrein is a zymogen of a trypsin-like serine protease and is present in plasma. The gene structure is similar to that of factor XI. Overall, the amino acid sequence of plasma kallikrein has 58% homology to factor XI. Proteolytic activation by factor XIIa at an internal I 389-R390 bond yields a heavy chain (371 amino acids) and a light chain (248 amino acids). The active site of plasma kallikrein is contained in the light chain. The light chain of plasma kallikrein reacts with protease 15 inhibitors, including alpha 2 macroglobulin and Cl-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability andvasodilation (for review, Coleman, R., "Contact Activation Pathway", Hemostasis and Thrombosis, pp. 103-122, Lippincott Williams & Wilkins (2001); Schmaier A. H., "Contact Activation", Thrombosis and Hemorrhage, pp. 105-128 (1998)).

Factor XIa inhibitor compounds are described in WO2013022814, WO 2013022814, WO 2013022818, WO 2013055984, WO2013056034, WO2013056060, WO2013118805, WO2013093484, WO2002042273, WO2002037937, WO2002060894, WO2003015715, WO2004002405, US20040180855, WO2004080971, WO2004094372, US20050228000, US20050282805, WO2005123680, US20090036438, US20120088758, US20060074103, WO2006062972, WO2006076246, US20060154915, US20090062287, US20060183771, WO2007070818, WO2007070816, WO2007070826, WO2008076805, WO2008157162, WO2009114677, WO2011100402, and WO2011100401.

SUMMARY OF THE INVENTION

The present invention relates to compounds of Formula I:

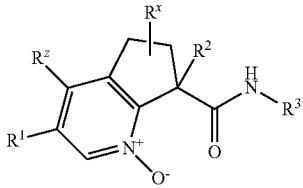

I or pharmaceutically acceptable salts thereof. The compounds of Formula I are selective Factor XIa inhibitors or dual inhibitors of Factor XIa and plasma kallikrein, and as such may be useful in the treatment, inhibition or amelioration of one or more disease states that could benefit from inhibition of Factor XIa or plasma kallikrein, including thromboses, embolisms, hypercoagulability or fibrotic changes. The compounds of this invention could further be used in combination with other therapeutically effective agents, including but not limited to, other drugs useful for the treatment of thromboses, embolisms, hypercoagulability or fibrotic changes. The invention furthermore relates to processes for preparing compounds of Formula I, and pharmaceutical compositions which comprise compounds of Formula I.

DETAILED DESCRIPTION OF THE INVENTION

The present invention relates to compounds of Formula I:

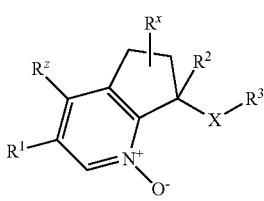

I wherein X is —(C=O)NH— or —NH(C=O)—;
$R^1$ is aryl, heteroaryl or $C_{3-6}$ cycloalkyl, wherein said aryl, heteroaryl and cycloalkyl groups are optionally substituted with one to three substituents independently selected from the group consisting of halo, nitro, cyano, oxo, $R^4$, $OR^4$, (C=O)$R^4$, (C=O)$OR^4$, $NR^4R^5$, NH(C=O)$R^4$, NH(C=O)$OR^4$, $C_{3-6}$ cycloalkyl and heteroaryl which is optionally substituted with $R^4$;
$R^2$ is hydrogen, hydroxy, halo or $C_{1-6}$ alkyl, wherein said alkly is optionally substituted with one or two substituents independently selected from the group consisting of halo, $OR^4$ or $C_{3-6}$ cycloalkyl;
$R^3$ is aryl, heteroaryl or $C_{3-10}$ cycloalkyl wherein said aryl, heteroaryl and cycloalkyl groups are optionally substituted with one to three substituents independently selected from the group consisting of halo, nitro, cyano, oxo, $R^4$, $OR^4$, (C=O)$R^4$, (C=O)$OR^4$, $NR^4R^5$, NH(C=O)$R^4$, NH(C=O)$OR^4$ and heteroaryl;
$R^4$ is hydrogen or $C_{1-6}$ alkyl, which is optionally substituted with one to three groups independently selected from the group consisting of halo and hydroxy;

$R^5$ is hydrogen or $C_{1-6}$ alkyl, which is optionally substituted with one to three groups independently selected from the group consisting of halo and hydroxy;
$R^x$ is hydrogen, hydroxy or halo;
$R^z$ is hydrogen, hydroxy, methoxy or halo;
or a pharmaceutically acceptable salt thereof.

An embodiment of the present invention relates to compounds of Formula Ia:

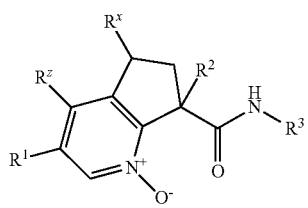

Ia wherein $R^1$ is phenyl, which is optionally substituted with one to three substituents independently selected from the group consisting of halo or heteroaryl which is optionally substituted with $R^4$;
$R^2$ is hydrogen, hydroxy, halo or $C_{1-6}$ alkyl, wherein said alkyl is optionally substituted with one or two substituents independently selected from the group consisting of halo, $OR^4$ or $C_{3-6}$ cycloalkyl;
$R^3$ is phenyl or $C_{3-10}$ cycloalkyl, wherein said phenyl and cycloalkyl groups are optionally substituted with one to three substituents independently selected from the group consisting of halo, cyano, oxo, $R^4$, $OR^4$, (C=O)$R^4$, (C=O)$OR^4$ and NH(C=O)$R^4$;
$R^4$ is hydrogen or $C_{1-6}$ alkyl, which is optionally substituted with one to three groups independently selected from the group consisting of halo and hydroxy,
$R^5$ is hydrogen or $C_{1-6}$ alkyl, which is optionally substituted with one to three groups independently selected from the group consisting of halo and hydroxy,
$R^x$ is hydrogen, hydroxy or halo;
$R^z$ is hydrogen, hydroxy, methoxy or halo;
or a pharmaceutically acceptable salt thereof.

The present invention also relates to compounds of Formula II:

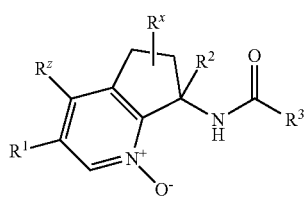

II wherein $R^1$ is aryl, heteroaryl or $C_{3-6}$ cycloalkyl, wherein said aryl, heteroaryl and cycloalkyl groups are optionally substituted with one to three substituents independently selected from the group consisting of halo, nitro, cyano, oxo, $R^4$, $OR^4$, (C=O)$R^4$, (C=O)$OR^4$, $NR^4R^5$, NH(C=O)$R^4$, NH(C=O)$OR^4$, $C_{3-6}$ cycloalkyl and heteroaryl which is optionally substituted with $R^4$;
$R^2$ is hydrogen, hydroxy, halo or $C_{1-6}$ alkyl, wherein said alkyl is optionally substituted with one or two substituents independently selected from the group consisting of halo, $OR^4$ or $C_{3-6}$ cycloalkyl;

$R^3$ is aryl, heteroaryl or $C_{3-10}$ cycloalkyl wherein said aryl, heteroaryl and cycloalkyl groups are optionally substituted with one to three substituents independently selected from the group consisting of halo, nitro, cyano, oxo, $R^4$, $OR^4$, $(C=O)R^4$, $(C=O)OR^4$, $NR^4R^5$, $NH(C=O)R^4$, $NH(C=O)OR^4$ and heteroaryl;
$R^4$ is hydrogen or $C_{1-6}$ alkyl, which is optionally substituted with one to three groups independently selected from the group consisting of halo and hydroxy;
$R^5$ is hydrogen or $C_{1-6}$ alkyl, which is optionally substituted with one to three groups independently selected from the group consisting of halo and hydroxy;
$R^x$ is hydrogen, hydroxy or halo;
$R^z$ is hydrogen, hydroxy, methoxy or halo;
or a pharmaceutically acceptable salt thereof.

The present invention relates to also relates to compounds of Formula I:

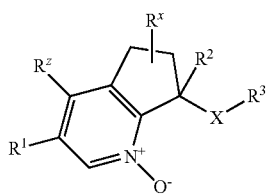

I wherein X is —(C=O)NH— or —NH(C=O)—;
$R^1$ is aryl, heteroaryl or $C_{3-6}$ cycloalkyl, wherein said aryl, heteroaryl and cycloalkyl groups are optionally substituted with one to three substituents independently selected from the group consisting of halo, nitro, cyano, oxo, $R^4$, $OR^4$, $(C=O)R^4$, $(C=O)OR^4$, $NR^4R^5$, $NH(C=O)R^4$, $NH(C=O)OR^4$, $C_{3-6}$ cycloalkyl and heteroaryl which is optionally substituted with $R^4$;
$R^2$ is hydrogen, hydroxy or halo;
$R^3$ is aryl, heteroaryl or $C_{3-10}$ cycloalkyl wherein said aryl, heteroaryl and cycloalkyl groups are optionally substituted with one to three substituents independently selected from the group consisting of halo, nitro, cyano, oxo, $R^4$, $OR^4$, $(C=O)R^4$, $(C=O)OR^4$, $NR^4R^5$, $NH(C=O)R^4$, $NH(C=O)OR^4$ and heteroaryl;
$R^4$ is hydrogen or $C_{1-6}$ alkyl, which is optionally substituted with one to three groups independently selected from the group consisting of halo and hydroxy;
$R^5$ is hydrogen or $C_{1-6}$ alkyl, which is optionally substituted with one to three groups independently selected from the group consisting of halo and hydroxy;
$R^x$ is hydrogen, hydroxy or halo;
$R^z$ is hydrogen, hydroxy, methoxy or halo;
or a pharmaceutically acceptable salt thereof.

In an embodiment of the invention, $R^1$ is phenyl, which optionally is substituted with two or three substituents independently selected from the group consisting of halo and heteroaryl. In a class of the embodiment, $R^1$ is phenyl, which optionally is substituted with halo and tetrazolyl. In another class of the embodiment, $R^1$ is phenyl, which optionally is substituted with three halo.

In an embodiment of the invention, $R^2$ is hydrogen. In another embodiment of the invention, $R^2$ is hydroxy. In another embodiment of the invention, $R^2$ is $CH_2$-cyclopropyl.

In an embodiment of the invention, $R^3$ is aryl, which is optionally substituted with one to three substituents independently selected from the group consisting of $(C=O)OR^4$ and $NH(C=O)R^4$. In a class of the embodiment, $R^3$ is aryl which is optionally substituted with $(C=O)OR^4$. In a class of the embodiment, $R^3$ is aryl which is optionally substituted with $NH(C=O)R^4$. In an subclass of the invention, $R^3$ is phenyl, which is optionally substituted with one to three substituents independently selected from the group consisting of $(C=O)OR^4$ and $NH(C=O)R^4$. In a subclass of the embodiment, $R^3$ is phenyl which is optionally substituted with $(C=O)OR^4$. In a subclass of the embodiment, $R^3$ is phenyl which is optionally substituted with $NH(C=O)R^4$. In another embodiment of the invention, $R^3$ is $C_{3-10}$ cycloalkyl, which is optionally substituted with one to three substituents independently selected from the group consisting of halo and $(C=O)OR^4$. In a class of the embodiment, $R^3$ is bicyclo[2.2.2]octanyl, which is optionally substituted with $(C=O)OR^4$. In another embodiment of the invention, $R^3$ is heteroaryl. In a class of the embodiment, $R^3$ is pyridinyl, pyrrolyl, thiophenyl, imidazolyl, pyrazolyl, oxazolyl, thiazolyl, triazolyl, thiadiazolyl, dithiazolyl, oxadiazolyl or tetrazolyl.

In an embodiment of the invention, $R^x$ is hydrogen. In another embodiment of the invention, $R^x$ is hydroxy. In another embodiment of the invention, $R^x$ is halo. In a class of embodiment of the invention, $R^x$ is fluoro.

Reference to the preferred classes and subclasses set forth above is meant to include all combinations of particular and preferred groups unless stated otherwise.

Specific embodiments of the present invention include, but are not limited to the compounds identified herein as Examples 1 to 20, or pharmaceutically acceptable salts thereof.

Also included within the scope of the present invention is a pharmaceutical composition which is comprised of a compound of Formula I, Formula Ia or Formula II as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention also includes compositions for inhibiting loss of blood platelets, inhibiting formation of blood platelet aggregates, inhibiting formation of fibrin, inhibiting thrombus formation, inhibiting embolus formation, and treating inflammatory disorders in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes compositions for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Compounds of the invention are Factor XIa inhibitors and may have therapeutic value in, for example, preventing coronary artery disease. The compounds are selective Factor XIa inhibitors or dual inhibitors of Factor XIa and plasma kallikrein.

It will be understood that, as used herein, references to the compounds of structural Formula I, Formula Ia and Formula II are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

If the compounds of Formula I, Formula Ia or Formula II simultaneously contain acidic and basic groups in the molecule the invention also includes, in addition to the salt forms mentioned, inner salts or betaines (zwitterions).

The present invention encompasses all stereoisomeric forms of the compounds of Formula I, Formula Ia and Formula II. Unless a specific stereochemistry is indicated, the present invention is meant to comprehend all such isomeric forms of these compounds. Centers of asymmetry that are present in the compounds of Formula I, Formula Ia and Formula II can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I, Formula Ia or Formula II or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. Unless a particular isomer, salt, solvate (including hydrates) or solvated salt of such racemate, enantiomer, diastereomer or tautomer is indicated, the present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable (e.g. $R^4$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I, Formula Ia and Formula II are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Reference to the compounds of this invention as those of a specific formula or embodiment, e.g., Formula I, Formula Ia or Formula II or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Except where noted herein, the term "alkyl" is intended to include both branched- and straight-chain saturated aliphatic hydrocarbon groups having the specified number of carbon atoms. Commonly used abbreviations for alkyl groups are used throughout the specification, e.g. methyl, may be represented by conventional abbreviations including "Me" or CH$_3$ or a symbol that is an extended bond as the terminal group, e.g.

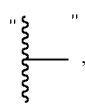

ethyl may be represented by "Et" or CH$_2$CH$_3$, propyl may be represented by "Pr" or CH$_2$CH$_2$CH$_3$, butyl may be represented by "Bu" or CH$_2$CH$_2$CH$_2$CH$_3$, etc. "C$_{1-4}$ alkyl" (or "C$_1$-C$_4$ alkyl") for example, means linear or branched chain alkyl groups, including all isomers, having the specified number of carbon atoms. For example, the structures

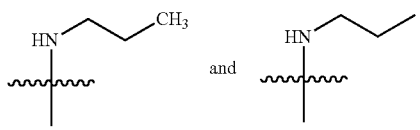

have equivalent meanings. C$_{1-4}$ alkyl includes n-, iso-, sec- and t-butyl, n- and isopropyl, ethyl and methyl. If no number is specified, 1-4 carbon atoms are intended for linear or branched alkyl groups.

Except where noted herein, "alkanol" is intended to include aliphatic alcohols having the specified number of carbon atoms, such as methanol, ethanol, propanol, etc., where the —OH group is attached at any aliphatic carbon, e.g., propan-1-ol, propan-2-ol, etc.

Except where noted, the term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, bicyclo[2.2.2]octanyl, and so on.

Except where noted, the term "halogen" or "halo" means fluorine, chlorine, bromine or iodine.

Except where noted, the term "heteroaryl", as used herein, represents a stable monocyclic, bicyclic or tricyclic ring of up to 10 atoms in each ring, wherein at least one ring is aromatic, and at least one ring contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, tetra-hydroquinoline and 3-oxo-3, 4dihydro-2Nbenzo[b][1,4]thiazine. If the heteroaryl contains nitrogen atoms, it is understood that the corresponding N-oxides thereof are also encompassed by this definition.

Except where noted, the term "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl and indanyl.

"Celite®" (Fluka) diatomite is diatomaceous earth, and can be referred to as "celite".

Except where noted herein, structures containing substituent variables such as variable "R" below:

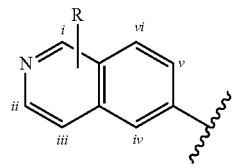

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also includes derivatives of the compounds of Formula I, Formula Ia and Formula II, acting as prodrugs and solvates. Prodrugs, following administration to the patient, are converted in the body by normal metabolic or chemical processes, such as through hydrolysis in the blood, to the compound of Formula 1, Formula Ia or Formula II. Such prodrugs include those that demonstrate enhanced bioavailability, tissue specificity, and/or cellular delivery, to improve drug absorption of the compound of Formula I, Formula Ia or Formula II. The effect of such prodrugs may result from modification of physicochemical properties such as lipophilicity, molecular weight, charge, and other physicochemical properties that determine the permeation properties of the drug.

The preparation of pharmaceutically acceptable salts from compounds of the Formula I, Formula Ia and Formula II capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula I, Formula Ia and Formula II form stable alkali metal, alkaline earth metal or optionally substituted ammonium salts. If the compounds of the Formula I, Formula Ia and Formula II have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments containing at least one compound of the Formula I or Formula Ia and/or of a pharmaceutically acceptable salt of the compound of the Formula I, Formula Ia or Formula II and/or an optionally stereoisomeric form of the compound of the Formula I, Formula Ia or Formula II or a pharmaceutically acceptable salt of the stereoisomeric form of the compound of Formula I, Formula Ia or Formula II, together with a pharmaceutically suitable and pharmaceutically acceptable vehicle, additive and/or other active substances and auxiliaries.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, humans, sheep, horses, cattle, pigs, dogs, cats, rats, and mice.

Factor XIa or dual Factor XIa/plasma kallikrein inhibition are useful not only in the anticoagulant therapy of individuals having thrombotic conditions, but are useful whenever inhibition of blood coagulation is required such as to prevent coagulation of stored whole blood and to prevent coagulation in other biological samples for testing or storage. Thus, the Factor XIa or dual Factor XIa/plasma kallikrein inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

The compounds of the invention may also be kallikrein inhibitors and especially useful for treatment of hereditary angioedema.

Examples of devices that come into contact with blood include vascular grafts, stents, orthopedic prosthesis, cardiac prosthesis, and extracorporeal circulation systems.

The medicaments according to the invention can be administered by oral, inhalative, rectal or transdermal administration or by subcutaneous, intraarticular, intraperitoneal or intravenous injection. Oral administration is preferred. Coating of stents with compounds of Formula I, Formula Ia or Formula II and other surfaces which come into contact with blood in the body is possible.

The invention also relates to a process for the production of a medicament, which comprises bringing at least one compound of Formula I, Formula Ia or Formula II into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor XIa inhibitors or dual Factor XIa/plasma kallikrein inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor XIa inhibitors or dual Factor XIa/plasma kallikrein inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the Factor XIa inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/mL, e.g. 0.1 mg/mL, 0.3 mg/mL, and 0.6 mg/mL, and administered in amounts per day of between 0.01 mL/kg patient weight and 10.0 mL/kg patient weight, e.g. 0.1 mL/kg, 0.2 mL/kg, 0.5 mL/kg. In one example, an 80 kg patient, receiving 8 mL twice a day of an intravenous formulation having a concentration of active ingredient of 0.5 mg/mL, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of the Formula I, Formula Ia and Formula II can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor XIa inhibitors or dual Factor XIa/plasma kallikrein inhibitors can also be co-administered with suitable anticoagulants, including, but not limited to, other Factor XIa inhibitors, thrombin inhibitors, thrombin receptor antagonists, factor VIIa inhibitors, factor Xa inhibitors, factor IXa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor XIa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO@), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; inhibitors of glucose uptake, such as sodium-glucose transporter (SGLT) inhibitors and its various isoforms, such as SGLT-1, SGLT-2 (e.g., ASP-1941, TS-071, BI-10773, tofogliflozin, LX-4211, canagliflozin, dapagliflozin, ertugliflozin, ipragliflozin, remogliflozin and sotagliflozin), and SGLT-3; or with other drugs beneficial for the prevention or the treatment of the abovementioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor XIa inhibitors or Factor XIa/plasma kallikrein inhibitors of the invention in combination with other suitable anti-platelet agents, anticoagulation agents, or thrombolytic agents may be the same as those doses of Factor XIa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of each of the compounds when administered individually as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

For purposes of this specification, the following abbreviations have the indicated meanings:

LIST OF ABBREVIATIONS

ACN=acetonitrile
AcOH or HOAc=acetic acid
aq=aqueous
Boc=tert-butoxycarbonyl
DMF=dimethylformamide
DCM=dichloromethane
DIAD=Diisopropyl azodicarboxylate
DIEA=N,N-Diisopropylethylamine
DIPEA=N,N-Diisopropylethylamine
DMAP=N,N-dimethylaminopyridine
dppf=1,1'-Bis(diphenylphosphino)ferrocene
EtOAc=ethyl acetate
EtOH=ethanol
h or hr=hour
Hex=Hexanes
HPLC=High Pressure Liquid Chromatography
RP HPLC=Reverse Phase High Pressure Liquid Chromatography
LCMS=Liquid chromatography-mass spectrometry
LHMDS=lithium hexamethyldisilazide
LiOH=lithium hydroxide
Me=methyl
MeOH=methanol
min=minute
MS=mass spectrometry
mCPBA=meta-chloroperoxybenzoic acid
NCS=N-chlorosuccinimide
rt or RT=room temperature
THF=tetrahydrofuran
satd=saturated
SEM=2-(trimethylsilyl)ethoxymethyl
SFC=supercritical fluid chromatography
SM=Starting material
TBAF=Tetra-n-butylammonium fluoride
TBS=tert-butyldimethylsilyl
TEA=Triethylamine
TFA=Trifluoroacetic acid
Vac=Vacuum
HATU=2-(1H-7-Azabenzotriazol-1-yl)-1,1,3,3-tetramethyluronium hexafluorophosphate Methanaminium Also, TLC is thin layer chromatography; Ts is tosyl; UV is ultraviolet; W is watts; wt. % is percentage by weight; ° C. is degrees Celsius; % w/v is percentage in weight of the former agent relative to the volume of the latter agent.

LCMS conditions: column: SUPELCO Ascentis Express C18 3×100 mm, 2.7 μm. Solvent system: A—0.05% TFA in water and B—0.05% TFA in Acetonitrile. Gradient condition: 10% B to 99% B in 3.5 min.

SCHEME 1

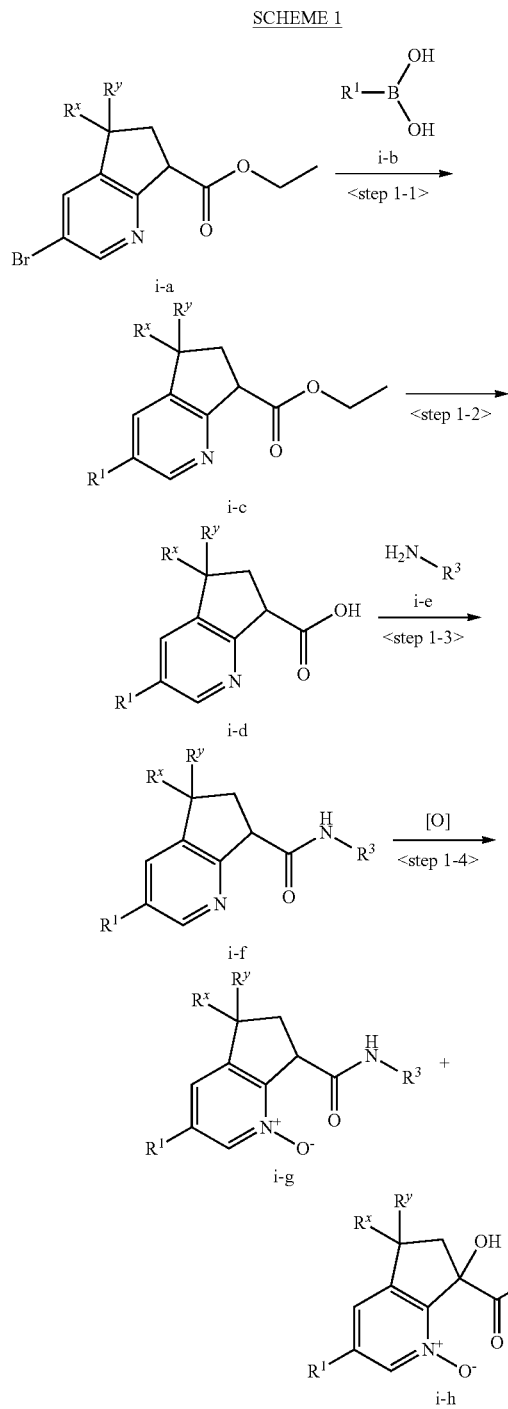

<Step 1-1>

A compound represented by formula (i-c) can be produced using a method commonly referred to as the Suzuki coupling reaction (Miyaura, Norio; Suzuki, Akira; Chemical Reviews (1996), 95, 2457-2483). Intermediates of type (i-a) can be treated with a boronic acid of type $R^1$—$B(OH)_2$ (i-b), or alternatively, a boronate ester of type $R^1$—$B(OR)_2$, in the presence of a suitable palladium catalyst, such as 1,1'-bis (diphenylphosphino)ferrocene palladium(II) dichloride, or the like, and a mild base, such as sodium carbonate, sodium phosphate tribasic, or the like. The reaction is usually performed in a suitable degassed mixture of an inert organic solvent, such as toluene, ethanol or dioxane, and water at elevated temperatures, generally between 70° C. and the boiling temperature of the solvent mixture, for a period of 3-24 hours. Alternatively, those skilled in the art can perform the Suzuki reaction described above in a suitable vessel that enables heating in a microwave reactor to superheated reaction temperatures that can reduce reaction times to between 1 minute and 1 hour. Alternatively, the reaction may be performed at room temperature using a suitable palladium precatalyst according to conditions recently reported in the literature (Kinzel, Tom; Zhang, Yong; Buchwald, Stephen L. Journal of the American Chemical Society (2010), 132, 14073-14075).

<Step 1-2>

A compound represented by formula (i-d) may be produced by allowing the intermediate (i-c) to react with a base such as lithium hydroxide, sodium hydroxide, or potassium hydroxide by a process well-known to those skilled in the art. The reaction can proceed in a suitable solvent such as THF, water, methanol, or ethanol, or mixtures thereof. This process can be carried out at temperatures between room temperature and the reflux temperature of the solvent for reaction times between several minutes to several hours.

<Step 1-3>

A compound represented by formula (i-f) may be produced by allowing the intermediate (i-d) to react with a properly substituted amine (i-e) by a well-known process or a process similar to that described in published documents, for example, Organic synthesis IV, Acids, amino acids, and peptides, pp. 191-309, 1992, Maruzen Co., Ltd., in the presence of a condensing agent such as 1,3-dicyclohexylcarbodiimide (DCC), 1-ethyl-3-(3'-dimethylaminopropyl) carbodiimide hydrochloride (WSC.HCl or EDC HCl), O-(7-azabenzotriazol-1-yl)-N,N,N',N'-tetramethyluronium hexafluorophosphate (HATU), benzotriazol-1-yloxy tris(dimethylamino)-phosphonium hexafluorophosphate (BOP reagent), or bis(2-oxo-3-oxazolidinyl)phosphinic chloride (BOP—Cl), in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethylformamide, or an alcoholic solvent, e.g., methanol, ethanol, or 2-propanol, in the presence or absence of a base such as triethylamine or N,N-diisopropylethyl amine at a temperature in the range of 0° C. to the solvent reflux temperature.

<Step 1-4>

A compound represented by formula (i-g) can be produced by allowing the suitably substituted pyridine of formula (i-f) to react with an oxidizing reagent such as hydrogen peroxide, mCPBA, oxone, dimethyldioxirane, or peracetic acid in a proper solvent including water, methylene chloride or acetic acid. The reaction is usually performed at a temperature between 0° C. to 70° C. in a time period ranging from a few minutes to a few days. In some cases, the use of a suitable catalyst, such as methylrhenium trioxide, may facilitate the oxidation reaction. Such a process or processes are similar to those described in published documents (For example, see, Deng, Lisheng Sundriyal, Sandeep; Rubio, Valentina; Shi, Zheng-zheng; Song. Yongcheng, Journal of Medicinal Chemistry (2009), 52(21), 6539-6542). In some examples, the hydroxylated analog (i-h) may also be observed during the oxidation reaction described above, or during earlier steps in the synthetic sequence.

SCHEME 2

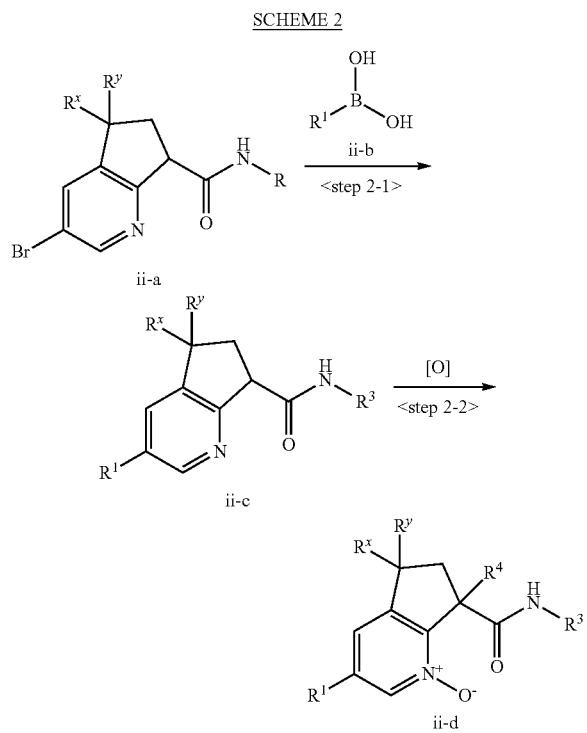

<Step 2-1>

A compound represented by formula (ii-c) can be produced using a method commonly referred to as the Suzuki coupling reaction (Miyaura, Norio; Suzuki, Akira; Chemical Reviews (1996), 95, 2457-2483). Intermediates of type (ii-a) can be treated with a boronic acid of type $R^1$—$B(OH)_2$ (ii-b), or alternatively, a boronate ester of type $R^1$—$B(OR)_2$, in the presence of a suitable palladium catalyst, such as 1,1'-bis(diphenylphosphino)ferrocene palladium(II) dichloride, or the like, and a mild base, such as sodium carbonate, sodium phosphate tribasic, cesium fluoride or the like. The reaction is usually performed in a suitable degassed mixture of an inert organic solvent, such as toluene, ethanol or dioxane, and water at elevated temperatures, generally between 70° C. and the boiling temperature of the solvent mixture, for a period of 3-24 hours. Alternatively, those skilled in the art can perform the Suzuki reaction described above in a suitable vessel that enables heating in a microwave reactor to superheated reaction temperatures that can reduce reaction times to between 1 minute and 1 hour. Alternatively, the reaction may be performed at room temperature using a suitable palladium precatalyst according to conditions recently reported in the literature (Kinzel, Tom; Zhang, Yong; Buchwald, Stephen L. Journal of the American Chemical Society (2010), 132, 14073-14075).

<Step 2-2>

A compound represented by formula (ii-d) can be produced by allowing the suitably substituted pyridine of formula (ii-c) to react with an oxidizing reagent such as hydrogen peroxide, mCPBA, oxone, dimethyldioxirane, or peracetic acid in a proper solvent including water, methylene chloride or acetic acid. The reaction is usually performed at a temperature between 0° C. to 70° C. in a time period ranging from a few minutes to a few days. In some cases, the use of a suitable catalyst, such as methylrhenium trioxide, may facilitate the oxidation reaction. Such a process or processes are similar to those described in published documents (For example, see, Deng, Lisheng; Sundriyal, Sandeep; Rubio, Valentina; Shi, Zheng-zheng; Song, Yongcheng. Journal of Medicinal Chemistry (2009), 52(21), 6539-6542).

SCHEME 3

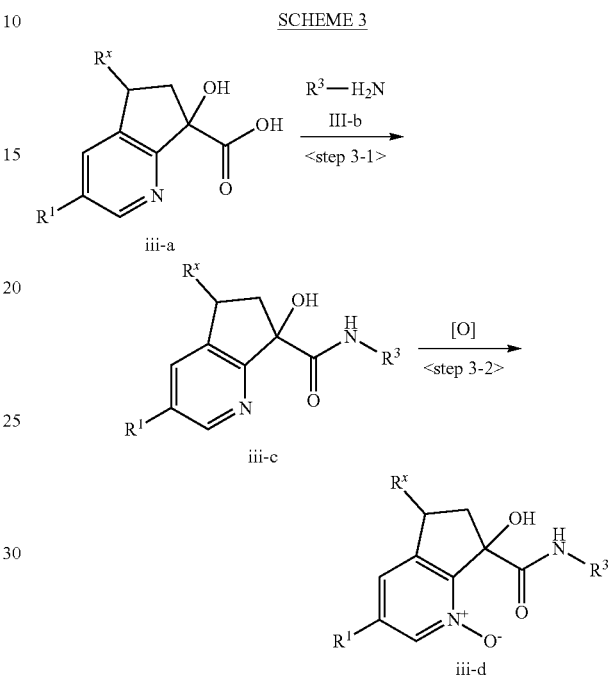

<Step 3-1>

A compound represented by formula (iii-c) may be produced by allowing the intermediate (iii-a) to react with a properly substituted amine (iii-b) by a well-known process or a process similar to that described in published documents, for example, Organic synthesis IV, Acids, amino acids, and peptides, pp. 191-309, 1992, Maruzen Co., Ltd., in the presence of a condensing agent such as 1,3-dicyclohexylcarbodiimide (DCC), 1-ethyl-3-(3'-dimethylaminopropyl)carbodiimide hydrochloride (WSC.HCl or EDC HCl), O-(7-azabenzotriazol-1-yl)-N,N,N',N'-tetramethyluronium hexafluorophosphate (HATU), benzotriazol-1-yloxy tris(dimethylamino)-phosphonium hexafluorophosphate (BOP reagent), or bis(2-oxo-3-oxazolidinyl)phosphinic chloride (BOP-Cl), in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethylformamide, or an alcoholic solvent, e.g., methanol, ethanol, or 2-propanol, in the presence or absence of a base such as triethylamine or N,N-diisopropylethyl amine at a temperature in the range of 0° C. to the solvent reflux temperature.

<Step 3-2>

A compound represented by formula (iii-d) can be produced by allowing the suitably substituted pyridine of formula (iii-c) to react with an oxidizing reagent such as hydrogen peroxide, mCPBA, oxone, dimethyldioxirane, or peracetic acid in a proper solvent including water, methylene chloride or acetic acid. The reaction is usually performed at a temperature between 0° C. to 70° C. in a time period ranging from a few minutes to a few days. In some cases, the use of a suitable catalyst, such as methylrhenium trioxide, may facilitate the oxidation reaction. Such a process or processes are similar to those described in published documents (For example, see, Deng, Lisheng; Sundriyal, Sandeep; Rubio, Valentina; Shi, Zheng-zheng; Song, Yongcheng, Journal of Medicinal Chemistry (2009), 52(21), 6539-6542).

SCHEME 4

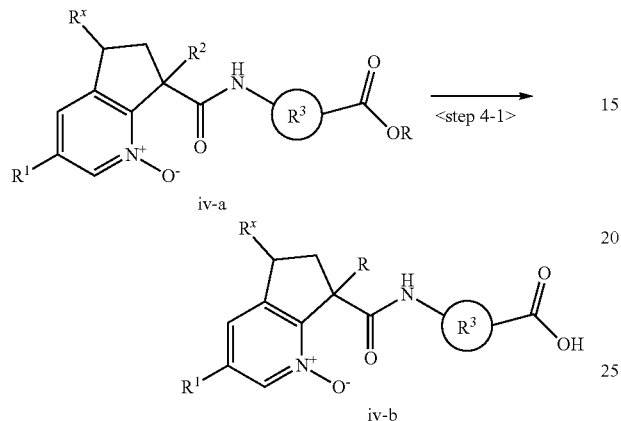

<Step 4-1>

In the specific case where a compound of the invention of type (iv-b) contains a carboxylic acid appended to $R^3$, an additional step may be required as illustrated in Scheme 4. The penultimate alkyl ester intermediate (iv-a) can be converted to the corresponding carboxylic acid following a well-known process or a process similar to that described in published documents, for example, Greene, T W., et. al., *Protective Groups in Organic Synthesis* (2007), 4th Ed. In some cases, this transformation may occur in the presence of an acid such as trifluoroacetic acid, formic acid, hydrochloric acid, or acetic acid in a solvent which is inactive to the reaction, such as a halogenated solvent, e.g., dichloromethane or chloroform, or an ethereal solvent, e.g., dioxane or tetrahydrofuran, at a temperature in the range of 0° C. to the solvent reflux temperature. In other cases, this process may occur in the presence of a base such as sodium hydroxide, potassium hydroxide, or lithium hydroxide in a solvent such as tetrahydrofuran, ethanol, or methanol, at a temperature in the range of 0° C. to the solvent reflux temperature.

The general reaction schemes as described above can generate compounds of formula (i-g), (i-h), (ii-d), (iii-d) and (iv-b) as a racemic mixtures or mixtures of several stereoisomers. A compound of formula (i-g), (i-h), (ii-d), (iii-d) or (iv-b) can be obtained as a single stereoisomer using a chiral resolution process such as chiral preparatory HPLC or chiral SFC.

SCHEME 5

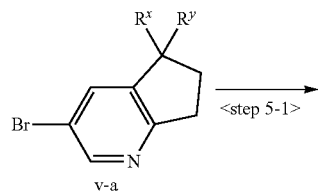

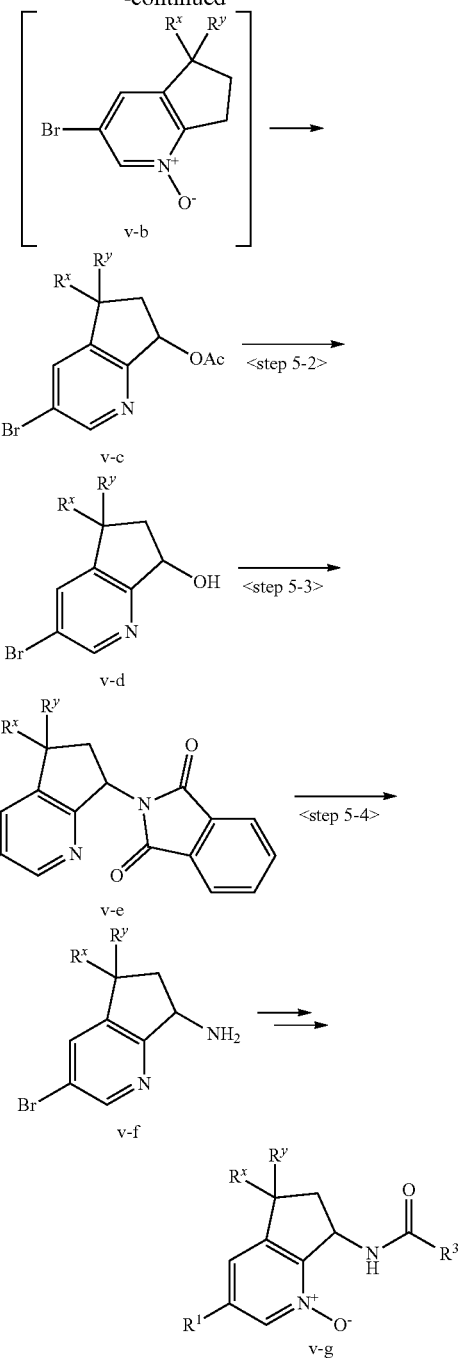

<Step 5-1>

A compound of type v-c can be prepared by treating compounds of type v-a with a suitable oxidant, such as hydrogen peroxide, to afford an intermediate of type v-b. The oxidation reaction described is typically performed in an inert solvent, such as acetic acid, at temperatures between room temperature and the boiling temperature of the solvent. The conversion of intermediate N-oxides of type v-b to compounds of type v-c can be performed in a two step-one pot procedure that initially involves treating the N-oxides (v-b) with a suitable acetylating agent, preferably acetic anhydride. The reaction is typically performed neat, and at elevated temperatures between 70° C. and the boiling temperature of the solvent.

<Step 5-2>
A compound of type v-d can be prepared under hydrolytic conditions that are well known to those skilled in the art. For example, compounds of type v-c can be treated with a suitable base, such as potassium carbonate or sodium hydroxide or the like, in a protic solvent, such as methanol, between 0° C. and room temperature.
<Step 5-3>
A compound of type v-e can be prepared by using the Mitsunobu reaction (reviewed in Castro, B. R. *Org. Reactions*, 2004, vol. 29) in which an alcohol of type v-d is reacted in the presence of phthalimide, triphenylphosphine and an activating agent such as DIAD, di-tert-butyl azodicarboxylate or the like. The reaction is performed in a suitable inert organic solvent such as benzene, toluene, THF or mixtures thereof, between 0° C. and room temperature, and the reaction can require overnight or longer periods for completion.
<Step 5-4>
A compound of type v-f can be prepared by treating compounds of type v-e with suitable nucleophile, such as hydrazine. The reaction is commonly performed in a protic solvent, such as EtOH or the like, typically between 50° C. and the boiling temperature of the solvent. The resulting amines of type v-f can be elaborated to compounds of the present invention (v-g).

Intermediates

Ethyl 3-bromo-6,7-dihydro-5H-cyclopenta[b]pyridine-7-carboxylate

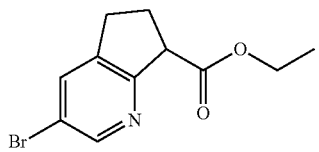

To a −78° C. solution of 3-bromo-6,7-dihydro-5H-cyclopenta[b]pyridine (4.95 g, 25.0 mmol) in THF (250 mL) was added a 1 M THF solution of LHMDS (62.5 mL, 62.5 mmol) dropwise via a syringe over 15 min. The resulting mixture was stirred at −78° C. for 65 min, then diethyl carbonate was added dropwise via a syringe at −78° C. The low temperature bath was removed and the reaction mixture was stirred with warming to room temperature over night. The reaction was quenched by addition of a saturated aq. solution of NH$_4$Cl (60 mL). The mixture was partitioned between brine (300 mL) and EtOAc (300 mL). The organic layer was dried over MgSO$_4$, filtered and concentrated in vacuo. The product was purified by silica gel chromatography (0-30% EtOAc in hexanes) to yield the product ethyl 3-bromo-6,7-dihydro-5H-cyclopenta[b]pyridine-7-carboxylate. MS (ESI) m/z 270.56 (M+H).

3-Bromo-6,7-dihydro-5H-cyclopenta[b]pyridine-7-carboxylic acid

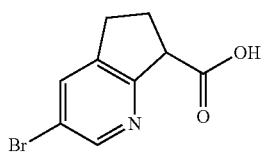 [SMILES: O=C(O)C1CCc2cc(Br)cnc21]

To a solution of ethyl 3-bromo-6,7-dihydro-5H-cyclopenta[b]pyridine-7-carboxylate (2.1 g, 7.77 mmol) in THF (10 mL) was added lithium hydroxide (4.66 mL, 9.33 mmol). The reaction mixture was heated at 50° C. for 30 min. After this time, LCMS showed conversion to the desired carboxylic acid. The solvent was removed under vacuum. The pH was adjusted to pH 3, then the mixture was extracted three time with EtOAc. The organic layers were combined, dried, filtered and concentrated to afford the lithium salt of 3-bromo-6,7-dihydro-5H-cyclopenta[b]pyridine-7-carboxylic acid. MS (ESI) m/z 244.02 (M+H).

Ethyl 3-bromo-5-((tert-butyldimethyl silyl)oxy)-6,7-dihydro-5H-cyclopenta[b]pyridine-7-carboxylate

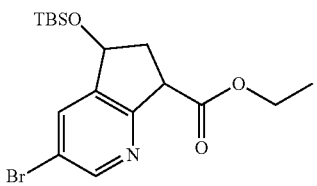 [SMILES: CCOC(=O)C1CC(O[Si](C)(C)C(C)(C)C)c2cc(Br)cnc21]

Step 1: 3-Bromo-6,7-dihydro-5H-cyclopenta[b]pyridin-5-ol

To 3-bromo-6,7-dihydro-5H-cyclopenta[b]pyridin-5-one (300 mg, 1.415 mmol) in ethanol (14 mL) was added sodium borohydride (107 mg, 2.83 mmol) portionwise at rt. The reaction mixture was stirred at rt for 2.5 h before 100% aqueous HCl was added. The volatiles were evaporated under vacuum, and the aqueous layer was treated with 1 N aqueous NaOH. It was then extracted twice with EtOAc (40.0 mL), and the combined organic layers were dried over Na$_2$SO$_4$, filtered and concentrated under vacuum to provide the title compound. MS (ESI) m/z 216.0 (M+H). The crude product was used directly in the next step.

Step 2: 3-Bromo-5-((tert-butyldimethylsilyl)oxy)-6,7-dihydro-5H-cyclopenta[b]pyridine To a mixture of 3-bromo-6,7-dihydro-5H-cyclopenta[b]pyridin-5-ol (303 mg, 1.42 mmol) in THF (9.4 mL) and DMF (4.7 mL) was added imidazole (145 mg, 2.12 mmol) followed by TBS-Cl (320 mg, 2.123 mmol) at rt. The reaction mixture was stirred at rt overnight, and the volatiles were evaporated under vacuum. The residue was diluted with EtOAc, washed with water, brine, dried over Na$_2$SO$_4$, filtered and concentrated under vacuum. The crude was purified by silica gel chromatography (24 g SiO$_2$) eluting with 0-25% EtOAc in hexanes to give 3-bromo-5-((tert-butyldimethylsilyl)oxy)-6,7-dihydro-5H-cyclopenta[b]pyridine. MS (ESI) m/z 330.2 (M+H).

Step 3: Ethyl 3-bromo-5-((tert-butyldimethylsilyl)oxy)-6,7-dihydro-5H-cyclopenta[b]pyridine-7-carboxylate To 3-bromo-5-((tert-butyldimethylsilyl)oxy)-6,7-dihydro-5H-cyclopenta[b]pyridine (409 mg, 1.246 mmol) in THF (12.5 mL) at −78° C. was added LHMDS (3.11 mL, 3.11 mmol) slowly via a syringe. The reaction mixture was stirred at the same temperature for 1 h, then diethyl carbonate (379 µl, 3.11 mmol) was added dropwise via a syringe.

The low temperature bath was removed, and the reaction mixture was warmed and stirred at rt overnight. Saturated aqueous NH₄Cl was added to quench the reaction, and the solvent was evaporated under vacuum. To the residue was added EtOAc, and the resulting mixture was washed with brine. The organic layer was dried over Na₂SO₄, filtered and concentrated under vacuum. The crude was purified by silica gel chromatography (24 g SiO₂) eluting with 0-100% EtOAc in hexanes to give ethyl 3-bromo-5-((tert-butyldimethylsilyl)oxy)-6,7-dihydro-5H-cyclopenta[b]pyridine-7-carboxylate. MS (ESI) m/z 400.2 (M+H).

tert-Butyl 4-(3-bromo-5,7-dihydroxy-6,7-dihydro-5H-cyclopenta[b]pyridine-7-carboxamido)benzoate

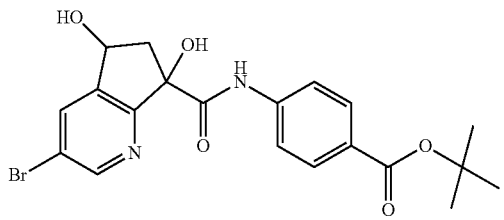 [SMILES: CC(C)(C)OC(=O)c1ccc(NC(=O)C2(O)CC(O)c3cc(Br)cnc32)cc1]

Step 1: 3-Bromo-5-((tert-butyldimethylsilyl)oxy)-6,7-dihydro-5H-cyclopenta[b]pyridine-7-carboxylic acid To a mixture of ethyl 3-bromo-5-((tert-butyldimethylsilyl)oxy)-6,7-dihydro-5H-cyclopenta[b]pyridine-7-carboxylate (9890 mg, 24.70 mmol) in THF (99 mL) was added aqueous 2 N LiOH (25 mL, 49.4 mmol) at rt. The reaction mixture was stirred at the same temperature overnight. The solvent was evaporated under vacuum, and the aqueous residue was acidified carefully with 3 N aqueous HCl until pH 3 was obtained. The mixture was extracted with EtOAc (2×, 150 mL). The combined organic layers were dried over Na₂SO₄, filtered and concentrated under vacuum. The crude 3-bromo-5-((tert-butyldimethylsilyl)oxy)-6,7-dihydro-5H-cyclopenta[b]pyridine-7-carboxylic acid was used directly in the next step. LCMS: m/z 372 [M+H]⁺.

Step 2: tert-Butyl 4-(3-bromo-5-((tert-butyldimethylsilyl)oxy)-6,7-dihydro-5H-cyclopenta[b]-pyridine-7-carboxamido)benzoate To a mixture of 3-bromo-5-((tert-butyldimethylsilyl)oxy)-6,7-dihydro-5H-cyclopenta[b]pyridine-7-carboxylic acid (4670 mg, 12.54 mmol), tert-butyl 4-aminobenzoate (2424 mg, 12.54 mmol) and DIPEA (6572 µl, 37.6 mmol) in THF (125 mL) was added HATU (4769 mg, 12.54 mmol). The reaction mixture was stirred at rt for 2 h and concentrated under vacuum. The residue was diluted with EtOAc and washed with saturated aqueous NaHCO₃. The organic layer was dried over Na₂SO₄, filtered and concentrated under vacuum. The crude was purified by silica gel chromatography, eluting with 0-20% EtOAc/hexanes, to give tert-butyl 4-(3-bromo-5-((tert-butyldimethylsilyl)oxy)-6,7-dihydro-5H-cyclopenta[b]pyridine-7-carboxamido)benzoate. LCMS: m/z 547 [M+H]⁺.

Step 3: tert-Butyl 4-(3-bromo-5,7-dihydroxy-6,7-dihydro-5H-cyclopenta[b]pyridine-7-carboxamido)benzoate A solution of tert-butyl 4-(3-bromo-5-((tert-butyldimethylsilyl)oxy)-6,7-dihydro-5H-cyclopenta[b]pyridine-7-carboxamido)benzoate (6790 mg, 12.40 mmol) and a 1 M THF solution of TBAF (25 mL, 25 mmol) in THF (62 mL) was stirred at it for 4 h. The reaction mixture was concentrated under vacuum. To the residue was added water and then the mixture was extracted with EtOAc (2×, 100 mL). The combined organic layers were dried over Na₂SO₄, filtered and concentrated under vacuum. The crude product was purified by silica gel chromatography, eluting with 0-90% EtOAc/hexanes, to give tert-butyl 4-(3-bromo-5,7-dihydroxy-6,7-dihydro-5H-cyclopenta[b]pyridine-7-carboxamido)benzoate. LCMS: m/z 449 [M+H].

tert-Butyl 4-(3-bromo-5,7-difluoro-6,7-dihydro-5H-cyclopenta[b]pyridine-7-carboxamido)benzoate tert-Butyl 4-(3-bromo-5-fluoro-7-hydroxy-6,7-dihydro-5H-cyclopenta[b]pyridine-7-carboxamido)benzoate

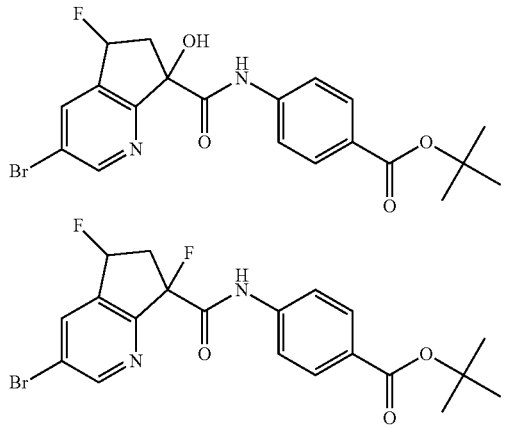

To a solution of triethylamine trihydrofluoride (407 µl, 2.422 mmol) and TEA (169 µl, 1.211 mmol) in DCM (60.5 mL) at rt was successively added difluoro(morpholino)sulfoniumtetrafluoroborate, XtalFluor-M (441 mg, 1.816 mmol) and tert-butyl 4-(3-bromo-5,7-dihydroxy-6,7-dihydro-5H-cyclopenta[b]pyridine-7-carboxamido)benzoate (described above) (544 mg, 1.211 mmol) in DCM (4 mL). The reaction mixture was stirred at rt for 24 h, quenched with 5% aqueous NaHCO₃, and stirred for an additional 15 min. The mixture was then extracted with DCM (2×, 20.0 mL), and the combined organic layers were dried over Na₂SO₄, filtered and concentrated under vacuum. The crude product was purified by silica gel chromatography, eluting with 0-100%, EtOAc/hexanes, to give tert-butyl 4-(3-bromo-5,7-difluoro-6,7-dihydro-5H-cyclopenta[b]pyridine-7-carboxamido)benzoate. LCMS: m/z 453 [M+H]⁺. tert-Butyl 4-(3-bromo-5-fluoro-7-hydroxy-6,7-dihydro-5H-cyclopenta[b]pyridine-7-carboxamido)-benzoate was also obtained. LCMS: m/z 451 [M+H]⁺.

3-(5-Chloro-2-(H-tetrazol-1-yl)phenyl)-7-hydroxy-6,7-dihydro-5H-cyclopenta[b]pyridine-7-carboxylic acid

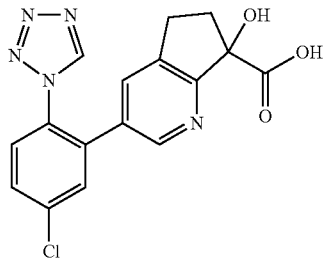 [SMILES: O=C(O)C1(O)CCc2cc(-c3cc(Cl)ccc3-n3cnnn3)cnc21]

Step 1: Ethyl 3-(2-amino-5-chlorophenyl-6,7-dihydro-5H-cyclopenta[b]pyridine-7-carboxylate A microwave vial was charged with ethyl 3-bromo-6,7-dihydro-5H-cyclopenta[b]pyridine-7-carboxylate (5 g, 18.51 mmol), 4-chloro-2-(4,4,5,5-tetramethyl-1,3,2-dioxaborolan-2-yl)aniline (5.87 g, 23.14 mmol), $PdCl_2(dppf)$ (2.71 g, 3.70 mmol) and $K_2CO_3$ (3.84 g, 27.8 mmol). The vial was capped and backfilled with $N_2$. After adding dioxane (50 mL) and water (10 mL), the mixture was heated at 100° C. for 2 h. The mixture was diluted with water and extracted with $CH_2Cl_2$/iPrOH (5:1, 2×50 mL). The organic phase was dried over $MgSO_4$, filtered, concentrated and purified on a silica gel column with 0-75% EtOAc/hexane to give ethyl 3-(2-amino-5-chlorophenyl)-6,7-dihydro-5H-cyclopenta[b]pyridine-7-carboxylate. LCMS: m/z 317.14 $[M+H]^+$.

Step 2: 3-(2-Amino-5-chlorophenyl)-7-hydroxy-6,7-dihydro-5H-cyclopenta[b]pyridine-7-carboxylic acid Sodium hydride (0.158 g, 3.95 mmol) was partially added to a solution of ethyl 3-(2-amino-5-chlorophenyl)-6,7-dihydro-5H-cyclopenta[b]pyridine-7-carboxylate (1.0 g, 3.16 mmol) in DMF (5 mL) at 0° C. The ice bath was removed then the mixture was stirred for 2 h. The mixture was neutralized with HCl (3.95 mL, 3.95 mmol) and stirred for 15 min. The mixture was purified by preparative reverse phase HPLC (C-18), eluting with acetonitrile/water, to give 3-(2-amino-5-chlorophenyl)-7-hydroxy-6,7-dihydro-5H-cyclopenta[b]pyridine-7-carboxylic acid. LCMS: m/z 305.12 $[M+H]^+$.

Step 3: 3-(5-Chloro-2-(1H-tetrazol-1-yl)phenyl)-7-hydroxy-6,7-dihydro-5H-cyclopenta[b]-pyridine-7-carboxylic acid Trimethyl orthoformate (1.045 mL, 9.45 mmol) was added to a solution of 3-(2-amino-5-chlorophenyl)-7-hydroxy-6,7-dihydro-5H-cyclopenta[b]pyridine-7-carboxylic acid (0.72 g, 2.363 mmol) in acetic acid (10 mL), followed by stirring at RT for 30 min. Sodium azide (0.461 g, 7.09 mmol) was added and the reaction mixture was stirred at RT overnight. The solvent was removed and the residue was purified by preparative reverse phase HPLC (C-18), eluting with acetonitrile/water, to give 3-(5-chloro-2-(H-tetrazol-1-yl)phenyl)-7-hydroxy-6,7-dihydro-5H-cyclopenta[b]pyridine-7-carboxylic acid. LCMS: m/z 358.09 $[M+H]f$.

3-Bromo-6,7-dihydro-5H-cyclopenta[b]pyridin-7-amine

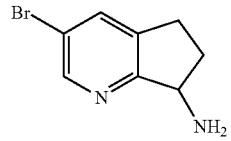 [SMILES: NC1CCc2cc(Br)cnc21]

Step 1: 3-Bromo-6,7-dihydro-5H-cyclopenta[b]pyridin-7-yl acetate

To a solution of 3-bromo-6,7-dihydro-5H-cyclopenta[b]pyridine (497 mg, 2.509 mmol) in acetic acid (1.5 ml) was added hydrogen peroxide (0.220 ml, 2.509 mmol). The resultant mixture was heated at 70° C. for 1.5 h, then cooled to ambient temperature, and additional hydrogen peroxide (0.220 ml, 2.509 mmol) was added. After heating at 70° C. for an additional 16 h, the reaction was quenched by addition of satd. aq. $NaHSO_3$ and partially concentrated in vacuo. The residue was treated with $Na_2CO_3(s)$ for 1 h then triturated with $CHCl_3$. The combined organic triturants were concentrated in vacuo and the resultant residue suspended in acetic anhydride (2.0 ml, 21.20 mmol) and heated at 90° C. for 16 h. The mixture was cooled to ambient temperature, concentrated in vacuo onto Celite®, and purified by flash chromatography on silica gel (gradient elution; 0%-100% EtOAc/hexanes as eluent) to provide the title compound. MS (ESI) m/z=256 [M+H].

Step 2: 3-Bromo-6,7-dihydro-5H-cyclopenta[b]pyridin-7-ol

To a solution of 3-bromo-6,7-dihydro-5H-cyclopenta[b]pyridin-7-yl acetate (261 mg, 1.02 mmol) in MeOH (3.4 mL) was added a solution of $K_2CO_3$ (352 mg, 2.55 mmol) in water (3.4 mL), and the resultant mixture was stirred at ambient temperature for 2 h. The reaction mixture was diluted with EtOAc, washed with $H_2O$ and brine. The organics were dried over $MgSO_4$, filtered, and concentrated in vacuo to provide the title compound. MS (ESI) m/z=214 [M+H].

Step 3: 2-(3-Bromo-6,7-dihydro-5H-cyclopenta[b]pyridin-7-yl)isoindoline-1,3-dione 3-Bromo-6,7-dihydro-5H-cyclopenta[b]pyridin-7-ol and phthalimide (106 mg, 0.719 mmol) were suspended in THF (4.4 mL), triphenylphosphine (214 mg, 0.818 mmol) was added, and the mixture cooled to 0° C. A solution of di-tert-butyl azodicarboxylate (181 mg, 0.785 mmol) in THF (1.5 mL) was added dropwise. After 5 min, the ice bath was removed, and the reaction mixture was warmed to rt and allowed to stir for 36 h. The reaction mixture was concentrated in vacuo, and the residue was purified by flash chromatography on silica gel (gradient elution; 0%-50% EtOAc/hexanes as eluent) to provide the title compound. MS (ESI) m/z=343 [M+H].

Step 4: 3-Bromo-6,7-dihydro-5H-cyclopenta[b]pyridin-7-amine 2-(3-Bromo-6,7-dihydro-5H-cyclopenta[b]pyridin-7-yl) isoindoline-1,3-dione (252 mg, 0.733 mmol) was suspended in EtOH (6 ml), and hydrazine hydrate (120 l, 2.42 mmol) was added. The resultant mixture was refluxed for 30 min, cooled to rt, and poured into 1N NaOH. The resulting mixture was extracted w/ DCM, and the combined organics were dried over MgSO₄, filtered, and concentrated in vacuo to provide the title compound. MS (ESI) m/z=213 [M+H].

Examples 1-4

4-[({3-[5-chloro-2-(1H-tetrazol-1-yl)phenyl]-1-oxido-6,7-dihydro-5H-cyclopenta[b]pyridin-7-yl}carbonyl)amino]benzoic acid (Example 1)

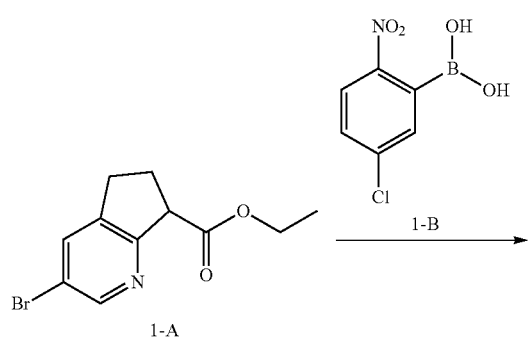

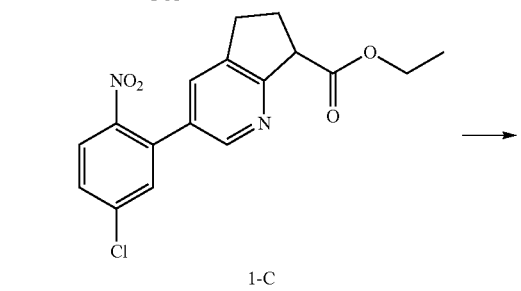

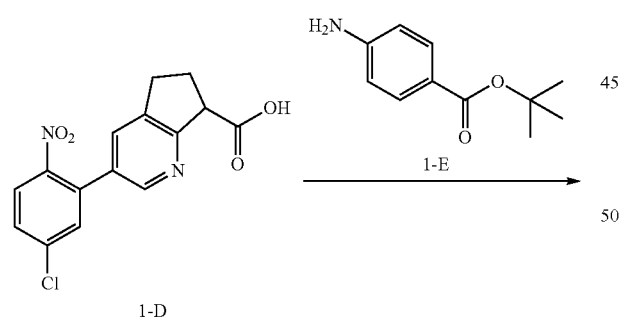

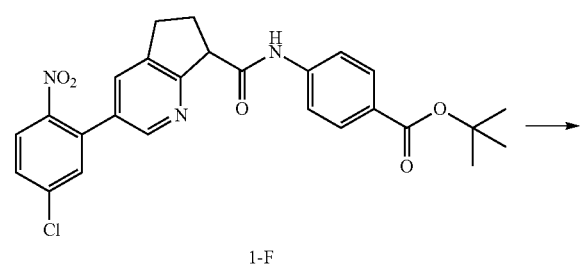

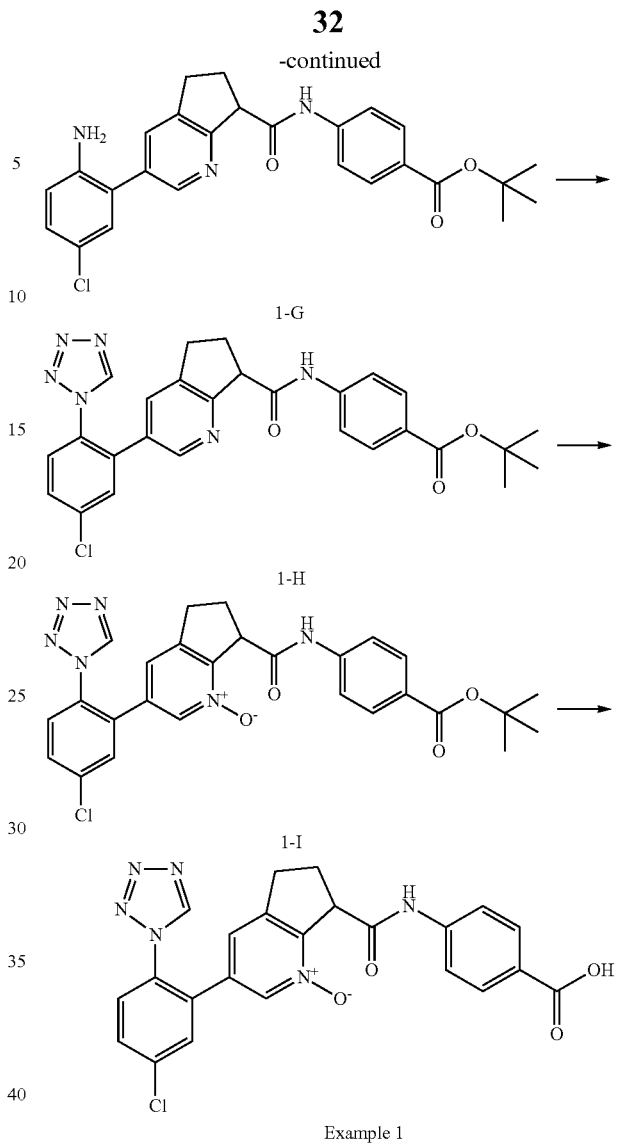

Example 1

Step 1: Ethyl 3-(5-chloro-2-nitrophenyl)-6,7-dihydro-5H-cyclopenta[b]pyridine-7-carboxylate A microwave vial was charged with ethyl 3-bromo-6,7-dihydro-5H-cyclopenta[b]pyridine-7-carboxylate (1-A) (1.0 g, 3.7 mmol), (5-chloro-2-nitrophenyl)boronic acid (1-B) (1.49 g, 7.40 mmol), 1,1'-bis(diphenylphosphino)ferrocene-palladium(II)dichloride dichloromethane complex (0.605 g, 0.740 mmol), THF (5 mL), and 2M aq. potassium phosphate tribasic (7.4 mL, 14.8 mmol). The reaction mixture was heated at 100° C. under microwave irradiation for 60 min. After this time, the reaction was not complete by LCMS analysis. More (5-chloro-2-nitrophenyl)boronic acid (1.491 g, 7.40 mmol) was added, and the reaction mixture was heated at 120° C. for 60 min. The mixture was cooled, filtered through celite, and the filtrates were partitioned between EtOAc and water. The organic phase was washed with brine, dried over sodium sulfate, and concentrated. Flash chromatography (80 g SiO₂, 0-100% EtOAc in hexane) gave the title compound. MS (ESI) m/z 349.22 (M+H).

Step 2: 3-(5-Chloro-2-nitrophenyl)-6,7-dihydro-5H-cyclopenta[b]pyridine-7-carboxylic acid (1-D)

To a solution of ethyl 3-(5-chloro-2-nitrophenyl)-6,7-dihydro-5H-cyclopenta[b]pyridine-7-carboxylate (1-C) in THF (10 mL) was added a 2M aq. solution of lithium hydroxide (1.38 mL, 2.77 mmol). The reaction mixture was heated at 50° C. for 15 min. After this time, the solvent was removed under vacuum and the resulting product was dried by adding toluene and evaporating off the toluene to give the lithium salt of the title compound. MS (ESI) m/z 319.10 (M+H). The crude product was used immediately in the next step without additional purification.

Step 3: tert-Butyl 4-(3-(5-chloro-2-nitrophenyl)-6,7-dihydro-5H-cyclopenta[b]pyridine-7-carboxamido) benzoate (1-F)

To a solution of 3-(5-chloro-2-nitrophenyl)-6,7-dihydro-5H-cyclopenta[b]pyridine-7-carboxylic acid (1-D) in DMF was added tert-butyl 4-aminobenzoate (1-E) (0.669 g, 3.46 mmol) and HATU (1.754 g, 4.61 mmol). The reaction mixture was stirred at rt for 1 hour. The mixture was quenched with water and extracted with EtOAc. The organic phase was washed with brine, dried over $Na_2SO_4$, filtered, and concentrated. The residue was purified by column chromatography on silica gel (80 g), eluting with EtOAc/hexane (0-80%), to afford the title compound. MS (ESI) m/z 494.25 (M+H).

Step 4: tert-Butyl 4-(3-(2-amino-5-chlorophenyl)-6,7-dihydro-5H-cyclopenta[b]pyridine-7-carboxamido)benzoate (1-G)

A mixture of tert-butyl-4-(3-(5-chloro-2-nitrophenyl)-6,7-dihydro-5H-cyclopenta[b]pyridine-7-carboxamido)benzoate (1-F) (0.914 g, 4.05 mmol), tin(II)chloride dihydrate (0.50 g, 1.0 mmol) in EtOAc (4 mL) and EtOH (2 mL) was heated at 50° C. for 3 hrs. After this time, LCMS showed the desired product. The mixture was concentrated, then the residue was diluted with EtOAc. A 1N aq. NaOH solution was added. The organic phase was removed and then washed with brine and dried over $Na_2SO_4$, filtered, and concentrated to afford the title compound. MS (ESI) m/z 466.33 (M+H). The crude product was used in the next step without additional purification.

Step 5: tert-Butyl 4-(3-(5-chloro-2-(H-tetrazol-1-yl)phenyl)-6,7-dihydro-5H-cyclopenta[b]-pyridine-7-carboxamido)benzoate (1-H)

tert-Butyl-4-(3-(2-amino-5-chlorophenyl)-6,7-dihydro-5H-cyclopenta[b]pyridine-7-carboxamido) benzoate (1-G) (0.48 g, 0.828 mmol) was combined with sodium azide (0.161 g, 2.483 mmol) followed by trimethoxymethane (0.263 g, 2.483 mmol) and acetic acid (6 mL). The reaction mixture was heated at 90° C. for 3 hr. LCMS showed formation of the desired product. The mixture was cooled to room temperature and solvent was removed under vacuum. The residue was diluted with ethyl acetate (50 mL), washed with water, brine, dried over $Na_2SO_4$, filtered and the solvent was evaporated under reduced pressure. The residue was purified by column chromatography on 40 g silica gel, eluting with EtOAc/hexane (0-50%) to give the title compound. MS (ESI) m/z 517.29 (M+H).

Step 6: 7-((4-(tert-Butoxycarbonyl)phenyl)carbamoyl)-3-(5-chloro-2-(1H-tetrazol-1-yl)phenyl)-6,7-dihydro-5H-cyclopenta[b]pyridine 1-oxide (1-I)

To a solution of tert-butyl 4-(3-(5-chloro-2-(1H-tetrazol-1-yl)phenyl)-6,7-dihydro-5H-cyclopenta[b]pyridine-7-carboxamido)benzoate (1-H) (140 mg, 0.271 mmol) in MeOH (3 mL) was added 35% hydrogen peroxide (0.237 mL, 2.71 mmol) and methyltrioxirhenium(VII) (33.7 mg, 0.135 mmol). The reaction mixture was stirred at room temperature for 1 hr. After this time, LCMS showed formation of the desired product. The mixture was diluted with EtOAc, washed with 10% aq. $NaHSO_3$. The organic phase was dried over $Na_2SO_4$, filtered, and concentrated. The product was purified using flash chromatography (0-100% EtOAc in hexane) to give the title compound. Some column fractions contained an over-oxidized byproduct. Further purification was accomplished using reverse phase HPLC (Gilson, Waters SunFire™ Prep $C_{18}$ OBD™ 5 μm 19×100 mm column, 0-100% MeCN in water with 0.05% TFA) to give the title compound at high purity. MS (ESI) m/z 533.40 (M+H).

Step 7: 4-[({3-[5-chloro-2-(1H-tetrazol-1-yl)phenyl]-1-oxido-6,7-dihydro-5H-cyclopenta[b]-pyridin-7-yl}-carbonyl)amino]benzoic acid (Example 1)

A solution of 7-((4-(tert-Butoxycarbonyl)phenyl)carbamoyl)-3-(5-chloro-2-(H-tetrazol-1-yl)phenyl)-6,7-dihydro-5H-cyclopenta[b]pyridine 1-oxide (75 mg, 0.141 mmol) and 1:1 TFA in DCM was stirred at room temperature for 1 hour. The solvent was removed to afford the crude product. A small amount of the crude product was purified using reverse phase HPLC (Gilson, Waters SunFire™ Prep $C_{18}$ OBD™ 5 μm 19×100 mm column, 0-100% MeCN in water with 0.05% TFA) to give the title compound at high purity. MS (ESI) m/z 477.16 (M+H). $^1$H NMR (DMSO-$d_6$) δ (ppm): 9.68 (s, 1H), 8.10 (s, 1H), 7.78-7.95 (m, 6H), 7.68 (dd, 2H), 7.05 (s, 1H), 4.40 (t, 1H), 2.98 (m, 2H), 2.35 (m, 2H).

The following compounds were prepared following procedures similar to those described above using appropriate starting materials and characterized by LCMS. For chiral, non-racemic compounds, resolution of the racemic mixture was accomplished by chiral SFC.

| Example | Name | Structure | LCMS [M + 1] |
|---|---|---|---|
| 2 | 7-((4-carboxybicyclo[2.2.2]octan-1-yl)carbamoyl)-3-(5-chloro-2-(1H-tetrazol-1-yl)phenyl)-6,7-dihydro-5H-cyclopenta[b]pyridine=1-oxide | 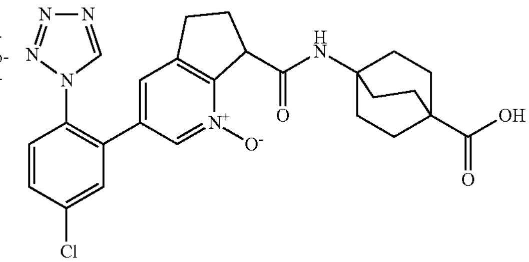 | 509.32 |
| 3 | 4-({[(7S)-3-(3-chloro-2,6-difluorophenyl)-1-oxido-6,7-dihydro-5H-cyclopenta[b]pyridin-b7-yl]carbonyl}amino)benzoic acid | 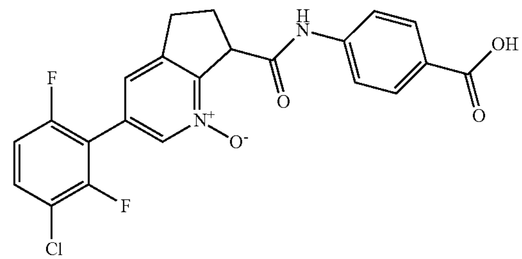 [SMILES: O=C(O)c1ccc(NC(=O)C2CCc3cc(-c4c(F)ccc(Cl)c4F)c[n+]([O-])c32)cc1] | 445.23 |
| 4 | 4-({[(7R)-3-(3-chloro-2,6-difluorophenyl)-1-oxido-6,7-dihydro-5H-cyclopenta[b]pyridin-7-yl]carbonyl}amino)benzoic acid | 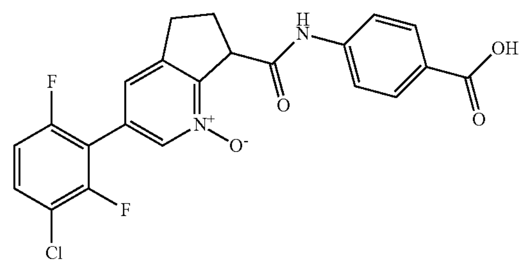 [SMILES: O=C(O)c1ccc(NC(=O)C2CCc3cc(-c4c(F)ccc(Cl)c4F)c[n+]([O-])c32)cc1] | 445.16 |

Examples 5-7

4-[{3-[5-chloro-2-(1H-tetrazol-1-yl)phenyl]-5-hydroxy-1-oxido-6,7-dihydro-5H-cyclopenta[b]pyridin-7-yl}carbonyl)amino]benzoic acid (Example 5—racemic mixture)

4-[({3-[5-chloro-2-(1H-tetrazol-1-yl)phenyl]-5-hydroxy-1-oxido-6,7-dihydro-5H-cyclopenta[b]pyridin-7-yl}carbonyl)amino]benzoic acid (Example 6—racemic mixture)

4-[{3-[5-chloro-2-(1H-tetrazol-1-yl)phenyl]-5-hydroxy-1-oxido-6,7-dihydro-5H-cyclopenta[b]pyridin-7-yl}carbonyl)amino]benzoic acid (Example 7—single stereoisomer)

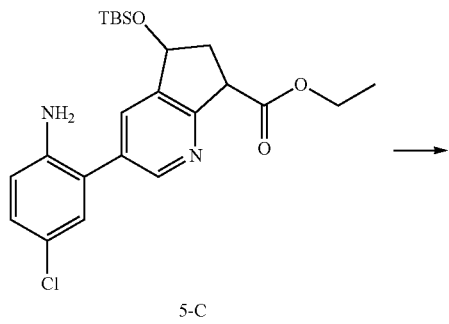

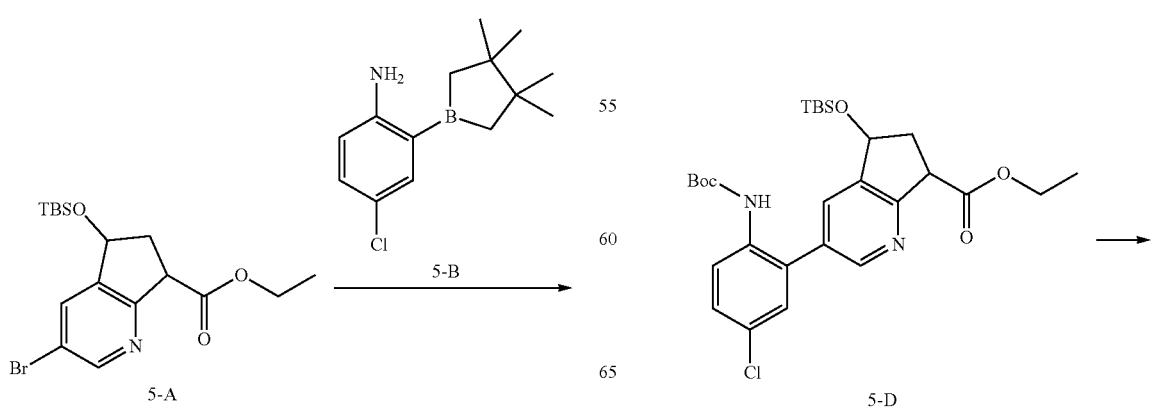

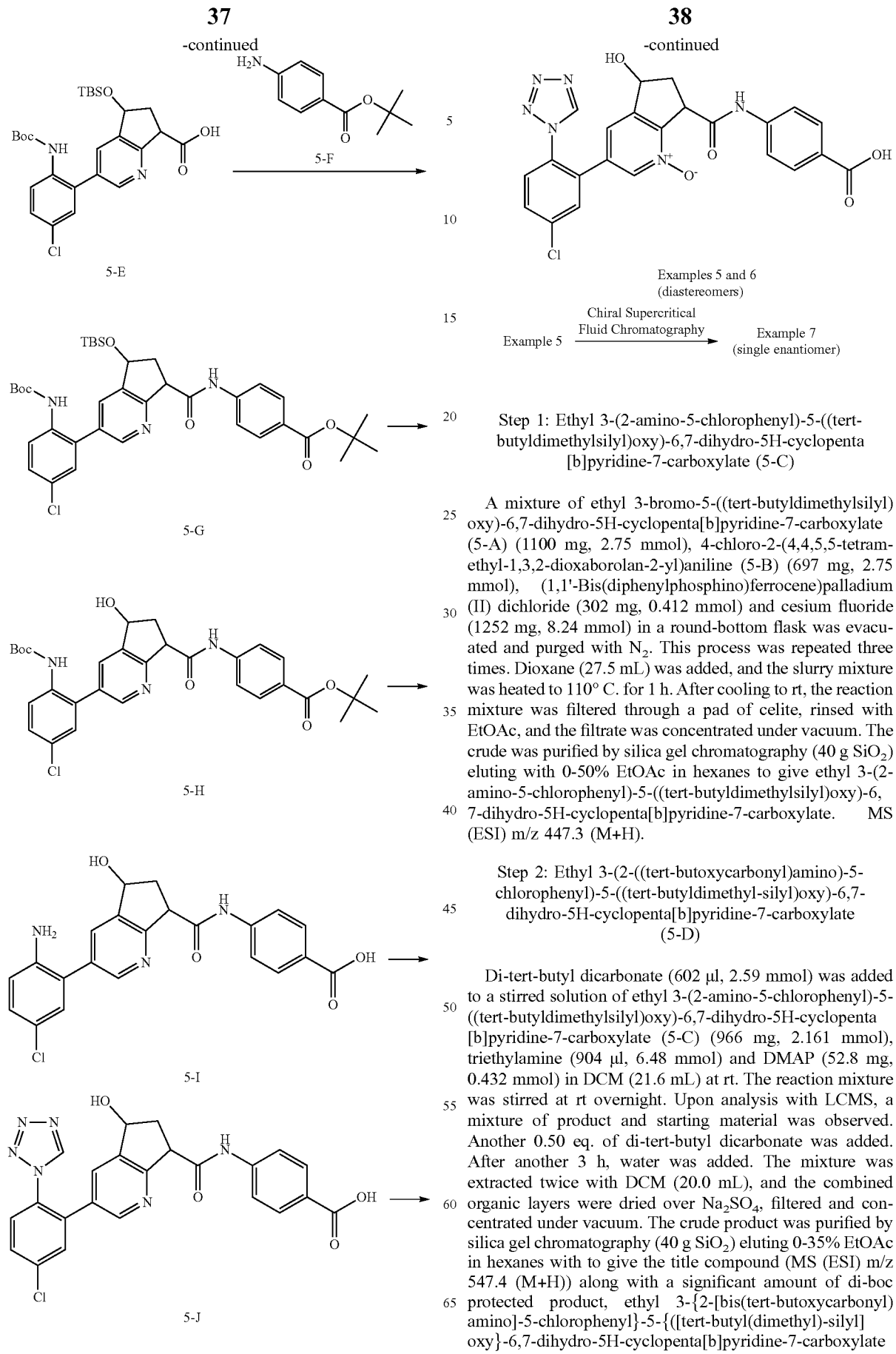

Step 1: Ethyl 3-(2-amino-5-chlorophenyl)-5-((tert-butyldimethylsilyl)oxy)-6,7-dihydro-5H-cyclopenta[b]pyridine-7-carboxylate (5-C)

A mixture of ethyl 3-bromo-5-((tert-butyldimethylsilyl)oxy)-6,7-dihydro-5H-cyclopenta[b]pyridine-7-carboxylate (5-A) (1100 mg, 2.75 mmol), 4-chloro-2-(4,4,5,5-tetramethyl-1,3,2-dioxaborolan-2-yl)aniline (5-B) (697 mg, 2.75 mmol), (1,1'-Bis(diphenylphosphino)ferrocene)palladium(II) dichloride (302 mg, 0.412 mmol) and cesium fluoride (1252 mg, 8.24 mmol) in a round-bottom flask was evacuated and purged with $N_2$. This process was repeated three times. Dioxane (27.5 mL) was added, and the slurry mixture was heated to 110° C. for 1 h. After cooling to rt, the reaction mixture was filtered through a pad of celite, rinsed with EtOAc, and the filtrate was concentrated under vacuum. The crude was purified by silica gel chromatography (40 g $SiO_2$) eluting with 0-50% EtOAc in hexanes to give ethyl 3-(2-amino-5-chlorophenyl)-5-((tert-butyldimethylsilyl)oxy)-6,7-dihydro-5H-cyclopenta[b]pyridine-7-carboxylate. MS (ESI) m/z 447.3 (M+H).

Step 2: Ethyl 3-(2-((tert-butoxycarbonyl)amino)-5-chlorophenyl)-5-((tert-butyldimethyl-silyl)oxy)-6,7-dihydro-5H-cyclopenta[b]pyridine-7-carboxylate (5-D)

Di-tert-butyl dicarbonate (602 μl, 2.59 mmol) was added to a stirred solution of ethyl 3-(2-amino-5-chlorophenyl)-5-((tert-butyldimethylsilyl)oxy)-6,7-dihydro-5H-cyclopenta[b]pyridine-7-carboxylate (5-C) (966 mg, 2.161 mmol), triethylamine (904 μl, 6.48 mmol) and DMAP (52.8 mg, 0.432 mmol) in DCM (21.6 mL) at rt. The reaction mixture was stirred at rt overnight. Upon analysis with LCMS, a mixture of product and starting material was observed. Another 0.50 eq. of di-tert-butyl dicarbonate was added. After another 3 h, water was added. The mixture was extracted twice with DCM (20.0 mL), and the combined organic layers were dried over $Na_2SO_4$, filtered and concentrated under vacuum. The crude product was purified by silica gel chromatography (40 g $SiO_2$) eluting 0-35% EtOAc in hexanes with to give the title compound (MS (ESI) m/z 547.4 (M+H)) along with a significant amount of di-boc protected product, ethyl 3-{2-[bis(tert-butoxycarbonyl)amino]-5-chlorophenyl}-5-{[(tert-butyl(dimethyl)-silyl]oxy}-6,7-dihydro-5H-cyclopenta[b]pyridine-7-carboxylate (MS (ESI) m/z 647.4 (M+H)). The product mixture was used in subsequent steps without further purification.

Step 3: 3-(2-((tert-Butoxycarbonylamino)-5-chlorophenyl-5-((tert-butyldimethyl-silyl)oxy)-6,7-dihydro-5H-cyclopenta[b]pyridine-7-carboxylic acid (5-E)

A mixture of ethyl 3-(2-((tert-butoxycarbonyl)amino)-5-chlorophenyl)-5-((tert-butyldimethylsilyl)oxy)-6,7-dihydro-5H-cyclopenta[b]pyridine-7-carboxylate (5-D) (772 mg, 1.411 mmol) and ethyl 3-{2-[bis(tert-butoxycarbonyl)amino]-5-chlorophenyl}-5-{[tert-butyl(dimethyl)silyl]oxy}-6,7-dihydro-5H-cyclopenta[b]pyri dine-7-carboxylate (913 mg, 1.411 mmol) in THF (7053 μl) was added LiOH (2821 μl, 5.64 mmol). The reaction mixture was stirred at rt for 4.5 h, and then the volatiles were evaporated under vacuum. The residue was diluted with EtOAc, acidified with 1 N aqueous HCl until pH of 4 was achieved. The mixture was washed with water. The organic layer was dried over $Na_2SO_4$, filtered and concentrated under vacuum to afford the title compound. MS (ESI) m/z 519.5 (M+H). The crude product, which contained a significant amount of di-boc material, was used directly in the next step without further purification.

Step 4: tert-Butyl 4-(3-(2-((tert-butoxycarbonylamino)-5-chlorophenyl)-5-((tert-butyldimethylsilyl)oxy)-6,7-dihydro-5H-cyclopenta[b]pyridine-7-carboxamido)benzoate (5-G)

To a mixture of 3-(2-((tert-butoxycarbonyl)amino)-5-chlorophenyl)-5-((tert-butyldimethyl-silyl)oxy)-6,7-dihydro-5H-cyclopenta[b]pyridine-7-carboxylic acid (5-E) (865 mg, 1.397 mmol), tert-butyl 4-aminobenzoate (5-F) (270 mg, 1.397 mmol) and DIPEA (732 μl, 4.19 mmol) in DMF (9313 μl) was added HATU (531 mg, 1.397 mmol) in one portion, and the reaction mixture was stirred at rt for 2 h. It was then quenched with water, and concentrated under vacuum. The aqueous residue was extracted twice with EtOAc (40.0 mL), and the combined organic layers were dried over $Na_2SO_4$, filtered and concentrated under vacuum. The crude was purified by silica gel chromatography, eluting with 0-70% EtOAc in hexanes to give a mixture of tert-butyl 4-{[(3-{2-[bis(tert-butoxycarbonyl)amino]-5-chlorophenyl}-5-{[tert-butyl(dimethyl)silyl]oxy}-6,7-dihydro-5H-cyclopenta[b]pyridin-7-yl)carbonyl]amino}benzoate (MS (ESI) m/z 794.7 (M+H)) and tert-butyl 4-(3-(2-((tert-butoxycarbonyl)amino)-5-chlorophenyl)-5-((tert-butyldimethylsilyl)oxy)-6,7-dihydro-5H-cyclopenta[b]pyridine-7-carboxamido)benzoate (MS (ESI) m/z 694.9 (M+H)). The product mixture was taken into the next step without additional purification.

Step 5: tert-Butyl 4-(3-(2-((tert-butoxycarbonyl)amino)-5-chlorophenyl)-5-hydroxy-6,7-dihydro-5H-cyclopenta[b]pyridine-7-carboxamido)benzoate (5-H)

To 413 mg of a mixture containing tert-butyl-4-(3-(2-((tert-butoxycarbonyl)amino)-5-chlorophenyl)-5-((tert-butyldimethylsilyl)-oxy)-6,7-dihydro-5H-cyclopenta[b]pyridine-7-carboxamido)benzoate (5-G) and tert-butyl 4-{[(3-{2-[bis(tert-butoxycarbonyl)amino]-5-chlorophenyl}-5-{[tert-butyl(dimethyl)silyl]oxy}-6,7-dihydro-5H-cyclopenta[b]pyridin-7-yl)carbonyl]amino}benzoate in THF (5.2 mL) was added a 1 M THF solution of TBAF (676 μl, 0.676 mmol) dropwise via a syringe. The reaction mixture was stirred at RT for 2 h before water was added to quench the reaction. The volatiles were evaporated under vacuum, and the residue was redissolved in EtOAc. After washing with satd. aqueous NaCl, the organic layer was dried over $Na_2SO_4$, filtered and concentrated under vacuum. The crude was purified by silica gel chromatography (24 g $SiO_2$) eluting with 0-70/o EtOAc in hexanes to give a mixture of the desired product tert-butyl 4-(3-(2-((tert-butoxycarbonyl)amino)-5-chlorophenyl)-5-hydroxy-6,7-dihydro-5H-cyclopenta[b]pyridine-7-carboxamido)benzoate (MS (ESI) m/z 580.4 (M+H)) and tert-butyl 4-{[(3-{2-[bis(tert-butoxycarbonyl)amino]-5-chlorophenyl}-5-hydroxy-6,7-dihydro-5H-cyclopenta[b]pyridin-7-yl)carbonyl]amino}benzoate. The product mixture was taken into the next step without further purification.

Step 6: 4-(3-(2-Amino-5-chlorophenyl)-5-hydroxy-6,7-dihydro-5H-cyclopenta[b]pyridine-7-carboxamido)benzoic acid (5-I)

To 351 mg of a mixture containing tert-butyl 4-(3-(2-((tert-butoxycarbonyl)amino)-5-chlorophenyl)-5-hydroxy-6,7-dihydro-5H-cyclopenta[b]pyridine-7-carboxamido)benzoate (5-H) and tert-butyl 4-{[(3-{2-[bis(tert-butoxycarbonyl)amino]-5-chlorophenyl}-5-hydroxy-6,7-dihydro-5H-cyclopenta[b]pyridin-7-yl)carbonyl]amino}benzoate in DCM (5.16 mL) was added TFA (3.00 mL, 38.9 mmol) dropwise via a syringe at rt. The reaction mixture was stirred at the same temperature for 1 h before concentrating under vacuum to afford the title compound. MS (ESI) m/z 424.2 (M+H). The crude residue was placed under high vacuum overnight and used without further purification.

Step 7: 4-(3-(5-Chloro-2-(1H-tetrazol-1-yl)phenyl)-5-hydroxy-6,7-dihydro-5H-cyclopenta[b]-pyridine-7-carboxamido)benzoic acid (5-J)

A mixture of 4-(3-(2-amino-5-chlorophenyl)-5-hydroxy-6,7-dihydro-5H-cyclopenta[b]pyridine-7-carboxamido)benzoic acid (5-1) (219 mg, 0.517 mmol), trimethyl orthoformate (171 μl, 1.55 mmol) and sodium azide (101 mg, 1.55 mmol) in AcOH (5.17 mL) was stirred at rt for 5 h. The solvent was evaporated under vacuum, and to the crude product was added EtOAc. The organic layer was carefully washed with saturated aqueous $NaHCO_3$ (adjusting the pH to 6), dried over $Na_2SO_4$, filtered and concentrated under vacuum. The crude product 4-(3-(5-chloro-2-(1H-tetrazol-1-yl)phenyl)-5-hydroxy-6,7-dihydro-5H-cyclopenta[b]pyridine-7-carboxamido)benzoic acid was used directly in the next step without further purification. MS (ESI) min 477.2 (M+H).

Step 8: 4-[({3-[5-Chloro-2-(1H-tetrazol-1-yl)phenyl]-5-hydroxy-1-oxido-6,7-dihydro-5H-cyclopenta[b]pyridin-7-yl}carbonyl)amino]benzoic acid (Example 5 and Example 6)

To a mixture of 4-(3-(5-chloro-2-(1H-tetrazol-1-yl)phenyl)-5-hydroxy-6,7-dihydro-5H-cyclopenta[b]pyridine-7-carboxamido)benzoic (5-L) (246 mg, 0.516 mmol) and methyltrioxorhenium(VII) (64.3 mg, 0.258 mmol) in MeOH (5.16 mL) was added 30% hydrogen peroxide (527 μl, 5.16 mmol). The reaction mixture was stirred at rt for 1 h before 10% aqueous $NaHSO_3$ was added to quench the reaction. MeOH was evaporated under vacuum. The aqueous mixture was extracted twice with EtOAc (50.0 mL), and the organic layers were dried over Na$_2$SO$_4$, filtered and concentrated under vacuum. The residue was purified by reverse phase HPLC (Waters Sunfire C18 column, 5u particle size, 19×100 mm, standard 10% ACN/H$_2$O to 37% ACN/H$_2$O buffering with 0.16% TFA, flow rte 25 mL/min over 15 min) to give Example 5 (MS (ESI) m/z 493.3 (M+H)) (LCMS retention time=0.79 min) and Example 6 ((MS (ESI) m/z 493.2 (M+H)) (LCMS retention time=0.77 min) as two separate racemic mixtures of 4-[({3-[5-chloro-2-(1H-tetrazol-1-yl)phenyl]-5-hydroxy-1-oxido-6,7-dihydro-5H-cyclopenta[b]-pyridin-7-yl}carbonyl)-amino]benzoic acid. The relative configurations of the two products were not assigned.

Step 9: 4-[({3-[5-Chloro-2-(1H-tetrazol-1-yl)phenyl]-5-hydroxy-1-oxido-6,7-dihydro-5H-cyclopenta[b]pyridin-7-yl}carbonyl)amino]benzoic acid (Example 7)

The more active racemic mixture from above, (Example 5), was subjected to chiral SFC using a 2×15 cm AD-H column eluting with 30% EtOH in CO$_2$ (100 bar, flow rate 60 mL/min). Two enantiomers of 4-[({3-[5-chloro-2-(1H-tetrazol-1-yl)phenyl]-5-hydroxy-1-oxido-5H-cyclopenta[b]pyridin-7-yl}carbonyl)amino]benzoic acid were separated, but only one (Example 7) was isolated. MS (ESI) m/z 493.3 (M+H) (SFC retention time=6.85 min). The absolute configuration was not assigned.

Examples 8-12

4-[({3-[5-Chloro-2-(1H-tetrazol-1-yl)phenyl]-5,7-dihydroxy-1-oxido-6,7-dihydro-5H-cyclopenta[b]pyridin-7-yl}carbonyl)amino]benzoic acid (Example 8)
4-[({3-[5-Chloro-2-(1H-tetrazol-1-yl)phenyl]-5,7-dihydroxy-1-oxido-6,7-dihydro-5H-cyclopenta[b]pyridin-7-yl}carbonyl)amino]benzoic acid (Example 9)
4-[({3-[5-Chloro-2-(1H-tetrazol-1-yl)phenyl]-5,7-dihydroxy-1-oxido-6,7-dihydro-5H-cyclopenta[b]pyridin-7-yl}carbonyl)amino]benzoic acid (Example 10)
4-[({3-[5-Chloro-2-(1H-tetrazol-1-yl)phenyl]-5,7-dihydroxy-1-oxido-6,7-dihydro-5H-cyclopenta[b]pyridin-7-yl}carbonyl)amino]benzoic acid (Example 11)
4-[({3-[5-Chloro-2-(1H-tetrazol-1-yl)phenyl]-5,7-dihydroxy-1-oxido-6,7-dihydro-5H-cyclopenta[b]pyridin-7-yl}carbonyl)amino]benzoic acid (Example 12)

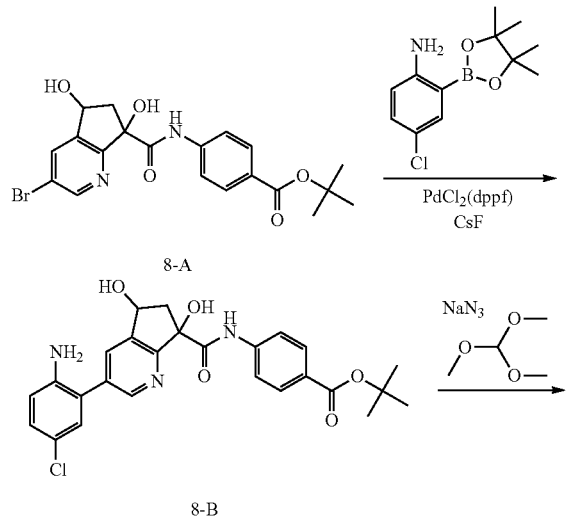

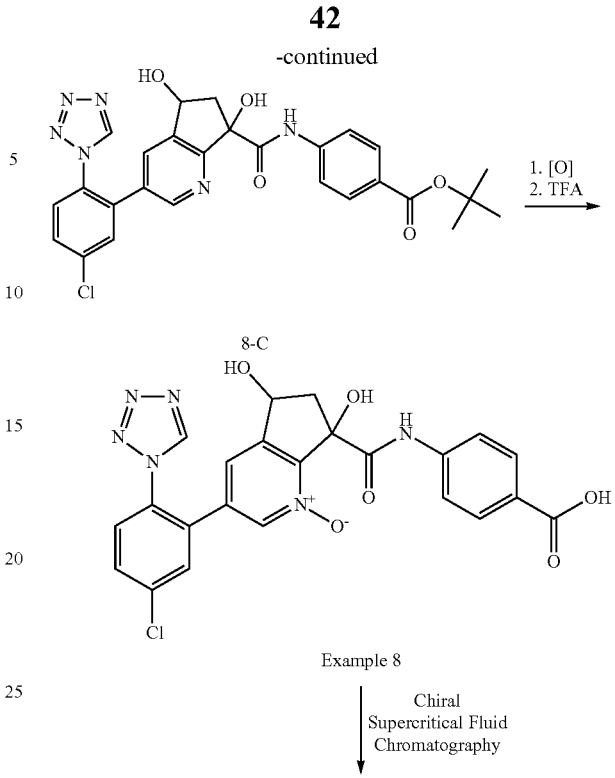

Example 8

Chiral Supercritical Fluid Chromatography

Examples 9-12

Step 1: tert-Butyl 4-(3-(2-amino-5-chlorophenyl)-5,7-dihydroxy-6,7-dihydro-5H-cyclopenta[b]-pyridine-7-carboxamido)benzoate (8-B)

A mixture of tert-butyl 4-(3-bromo-5,7-dihydroxy-6,7-dihydro-5H-cyclopenta[b]pyridine-7-carboxamido)benzoate (8-A) (1500 mg, 3.34 mmol), 4-chloro-2-(4,4,5,5-tetramethyl-1,3,2-dioxaborolan-2-yl)aniline (1100 mg, 4.34 mmol), PdCl$_2$(dppf) (366 mg, 0.501 mmol) and cesium fluoride (1521 mg, 10.02 mmol) in a round bottom flask were evacuated under vacuum and purged with N$_2$ (the process was repeated 3×). Dioxane (3.34E+04 µl) was then added, and the slurry mixture was heated to 110° C. for 1 h. After cooling to rt, the reaction mixture was filtered through a pad of celite, rinsed with EtOAc, and the filtrate was concentrated under vacuum. The crude was purified by silica gel chromatography, eluting with 0-100% EtOAc/Hexanes, to give tert-butyl 4-(3-(2-amino-5-chlorophenyl)-5,7-dihydroxy-6,7-dihydro-5H-cyclopenta[b]pyridine-7-carboxamido)benzoate (8-B). LCMS: m/z 496 [M+H]$^+$.

Step 2: tert-Butyl 4-(3-(5-chloro-2-(1H-tetrazol-1-yl)phenyl)-5,7-dihydroxy-6,7-dihydro-5H-cyclopenta[b]pyridine-7-carboxamido)benzoate (8-C)

A mixture of tert-butyl 4-(3-(2-amino-5-chlorophenyl)-5,7-dihydroxy-6,7-dihydro-5H-cyclopenta[b]pyridine-7-carboxamido)benzoate (8-B) (1570 mg, 3.17 mmol), trimethyl orthoformate (1050 µl, 9.50 mmol) and sodium azide (617 mg, 9.50 mmol) in AcOH (32 mL) was stirred at rt overnight. The solvent was evaporated under vacuum, and to the crude was added EtOAc. The organic layer was washed with satd. aqueous NaHCO$_3$, dried over Na$_2$SO$_4$, filtered and concentrated under vacuum. The crude product was purified by silica gel chromatography, eluting with 0-100% EtOAc/hexanes, to give tert-butyl 4-(3-(5-chloro-2-(1H-tetrazol-1-yl)phenyl)-5,7-dihydroxy-6,7-dihydro-5H-cyclopenta[b]pyridine-7-carboxamido)-benzoate (8-C). LCMS: m/z 549 [M+H].

Step 3: 4-[({3-[5-Chloro-2-(1H-tetrazol-1-yl)phenyl]-5,7-dihydroxy-1-oxido-6,7-dihydro-5H-cyclopenta[b]pyridin-7-yl}carbonyl)amino]benzoic acid (Example 8)

To a mixture of tert-butyl 4-(3-(5-chloro-2-(1H-tetrazol-1-yl)phenyl)-5,7-dihydroxy-6,7-dihydro-5H-cyclopenta[b]pyridine-7-carboxamido)benzoate (8-C) (1290 mg, 2.350 mmol) and methyltrioxorhenium (293 mg, 1.175 mmol) in MeOH (24 mL) was added hydrogen peroxide (2057 µl, 23.50 mmol). The reaction mixture was stirred at rt for 3.5 h before 10% aqueous NaHSO$_3$ was added to quench the reaction. The combined mixture was then extracted with EtOAc (2×, 50.0 mL), and the organic layers were dried over Na$_2$SO$_4$, filtered and concentrated under vacuum. The crude was used directly in the next step. LCMS: m/z 565 [M+H]$^+$. The N-oxide product was dissolved in DCM (7.00 mL) and 2,2,2-trifluoroacetic acid (7000 µl, 91 mmol) was added dropwise via a syringe. The reaction was stirred at rt for 1.5 h, and concentrated under vacuum. The residue was purified by RP HPLC (Gilson on a 19×100 mm, Waters XBridge C18 column, 5µ particle size, linear gradient, standard 5% ACN/H$_2$O to 100% ACN/H$_2$O buffering with 0.05% TFA @ flow rate 30 mL/min over 15 min) to give a mixture of four stereoisomers of 4-[((3-[5-chloro-2-(1H-tetrazol-1-yl)phenyl]-5,7-dihydroxy-1-oxido-6,7-dihydro-5H-cyclopenta[b]pyridin-7-yl) carbonyl)amino]benzoic acid (Example 8). LCMS: m/z 509 [M+H]$^+$.

Further purification by chiral SFC (step 1 separation of peak 3 and 4-IC (3×15 cm), 50% MeOH/CO$_2$, 100 bar, 55 ml/min; step 2 separation of peak 1 and 2-OZ—H (2×25 cm), 60% MeOH (0.1% DEA)/CO$_2$, 100 bar, 50 mL/min) furnished 4 chirally pure isomers with the following SFC retention times: (Example 9 Rt=3.63 min, Example 10 Rt=3.94 min, Example 11 Rt=8.20 min, Example 12 Rt=14.6 min).

Example 13-14

4-[({3-[5-Chloro-2-(1H-tetrazol-1-yl)phenyl]-5-fluoro-7-hydroxy-1-oxido-6,7-dihydro-5H-cyclopenta[b]pyridin-7-yl}carbonyl)amino]benzoic acid (Example 13)

4-[({3-[5-Chloro-2-(1H-tetrazol-1-yl)phenyl]-5-fluoro-7-hydroxy-1-oxido-6,7-dihydro-5H-cyclopenta[b]pyridin-7-yl}carbonyl)amino]benzoic acid (Example 14)

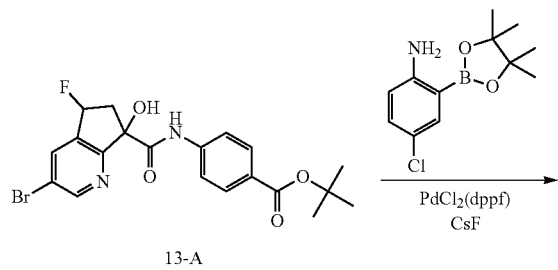

13-A

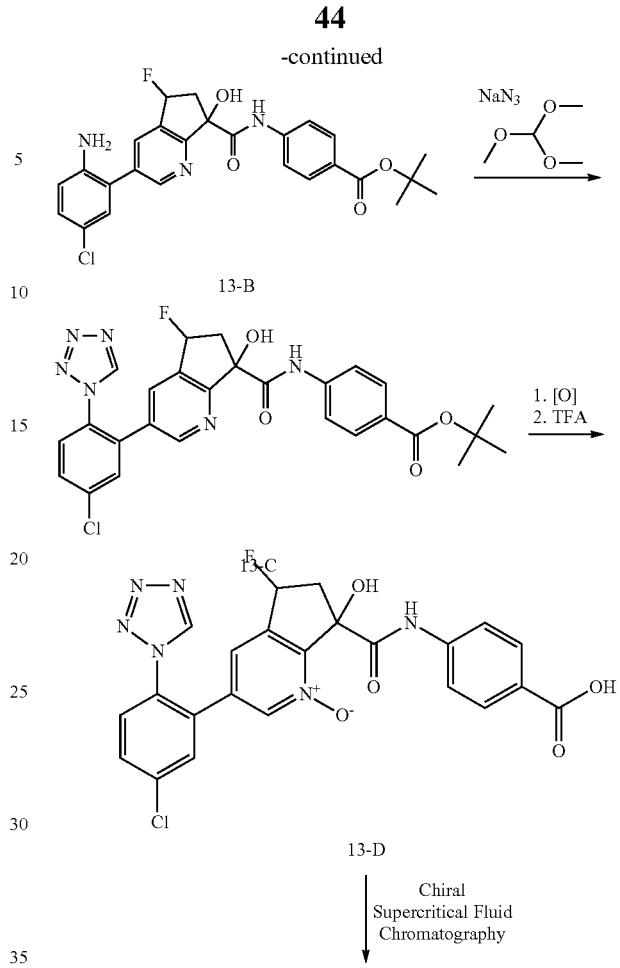

Examples 13-14

Examples 13 and 14 were synthesized using the procedure outlined above for the synthesis of Example 8 by replacing intermediate 8-A with 13-A. Purification by reverse-phase HPLC (Gilson on a 19×100 mm, Waters XBridge C18 column, 5µ particle size, linear gradient, standard 1% ACN/H$_2$O to 100% ACN/H$_2$O buffering with 0.05% TFA @ flow rate 30 mL/min over 15 min) afforded a mixture of two stereoisomers. LCMS: m/z 511 [M+H]$^+$. Further purification by chiral SFC (AS-H (2×15 cm), 35% MeOH/CO$_2$, 100 bar, 60 mL/min) furnished two separate stereoisomers of 4-[({3-[5-chloro-2-(1H-tetrazol-1-yl)phenyl]-5-fluoro-7-hydroxy-1-oxido-6,7-dihydro-5H-cyclopenta[b]pyridin-7-yl}carbonyl)amino]benzoic acid with the following SFC retention times (Rt=1.93 min (Example 13), Rt=2.68 min (Example 14)).

Examples 15-18

4-[({3-[5-Chloro-2-(1H-tetrazol-1-yl)phenyl]-5,7-difluoro-1-oxido-6,7-dihydro-5H-cyclopenta[b]pyridin-7-yl}carbonyl)amino]benzoic acid (Example 15)

4-[({3-[5-Chloro-2-(1H-tetrazol-1-yl)phenyl]-5,7-difluoro-1-oxido-6,7-dihydro-5H-cyclopenta[b]pyridin-7-yl}carbonyl)amino]benzoic acid (Example 16)

4-[({3-[5-Chloro-2-(1H-tetrazol-1-yl)phenyl]-5,7-difluoro-1-oxido-6,7-dihydro-5H-cyclopenta[b]pyridin-7-yl}carbonyl)amino]benzoic acid (Example 17)

4-[({3-[5-Chloro-2-(1H-tetrazol-1-yl)phenyl]-5,7-difluoro-1-oxido-6,7-dihydro-5H-cyclopenta[b]pyridin-7-yl}carbonyl)amino]benzoic acid (Example 18)

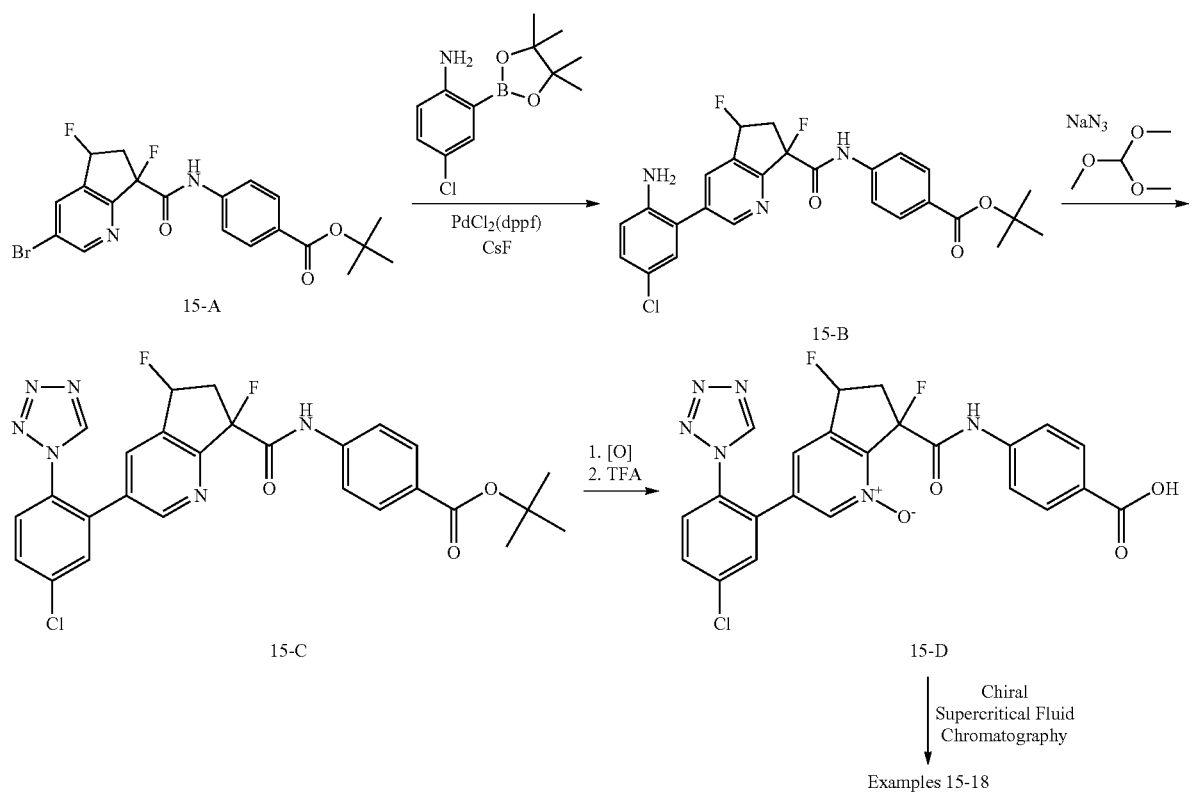

Examples 15-18 were synthesized using the procedure described above for Example 8 by replacing intermediate 8-A with 15-A. Reverse phase HPLC (Gilson, 19×100 mm, Waters XBridge C18 column, 5μ particle size, linear gradient, standard 5% ACN/H$_2$O to 100% ACN/H$_2$O buffering with 0.05% TFA @ flow rate 30 mL/min over 15 min) was utilized to give 15-D as a mixture of 4 stereoisomers. LCMS: m/z 513 [M+H]$^+$. Further purification by chiral SFC (IC (4.6×250 mm), 50% 2:1 MeOH:MeCN/CO$_2$, 100 bar, 2.1 mL/min) furnished four separated stereoisomers of 4-[({3-[5-chloro-2-(1H-tetrazol-1-yl)phenyl]-5,7-difluoro-1-oxido-6,7-dihydro-5H-cyclopenta[b]pyridin-7-yl}carbonyl)amino]benzoic acid with the following SFC retention times: (Example 15 Rt=2.78 min, Example 16 Rt=3.24 min, Example 17 Rt=4.43 min, Example 18 Rt$_4$=8.34 min).

Example 19

4-[({3-[5-Chloro-2-(1H-tetrazol-1-yl)phenyl]-7-hydroxy-1-oxido-6,7-dihydro-5H-cyclopenta[b]pyridin-7-yl}carbonyl)amino]benzoic acid

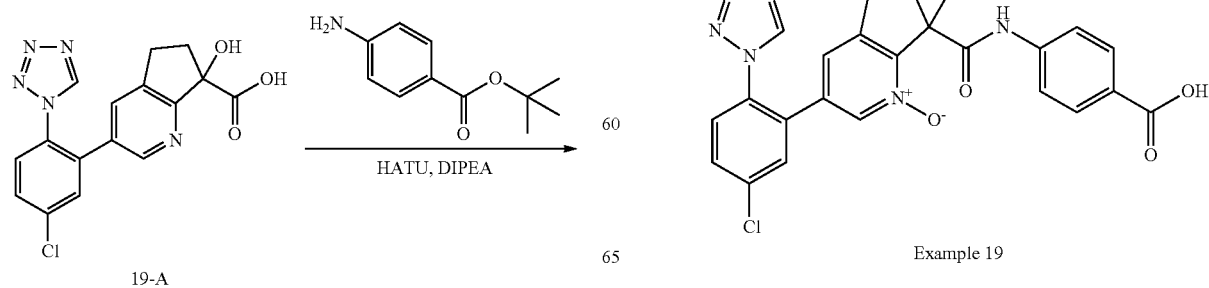

Step 1: tert-Butyl 4-(3-(5-chloro-2-(1H-tetrazol-1-yl)phenyl)-7-hydroxy-6,7-dihydro-5H-cyclopenta[b]pyridine-7-carboxamido)benzoate (19-B)

A solution of tert-butyl 4-aminobenzoate (0.101 g, 0.524 mmol) in DMF (2 mL) was added to a solution of 3-(5-chloro-2-(1H-tetrazol-1-yl)phenyl)-7-hydroxy-6,7-dihydro-5H-cyclopenta[b]-pyridine-7-carboxylic acid (19-A) (0.125 g, 0.349 mmol), Hunig's Base (0.061 mL, 0.349 mmol) and HATU (0.166 g, 0.437 mmol) in DMF (2 mL) at 0° C., followed by stirring at RT for 1 h. The DMF was removed and the residue was purified on a silica gel column with 0-75% EtOAc/hexane to give tert-butyl 4-(3-(5-chloro-2-(1H-tetrazol-1-yl)phenyl)-7-hydroxy-6,7-dihydro-5H-cyclopenta[b]pyridine-7-carboxamido)benzoate. LCMS: m/z 533.24 [M+H]$^+$.

Step 2: 4-(3-(5-Chloro-2-(1H-tetrazol-1-yl)phenyl)-7-hydroxy-6,7-dihydro-5H-cyclopenta[b]-pyridine-7-carboxamido)benzoic acid (19-C)

A solution of tert-butyl 4-(3-(5-chloro-2-(1H-tetrazol-1-yl)phenyl)-7-hydroxy-6,7-dihydro-5H-cyclopenta[b]pyridine-7-carboxamido)benzoate (19-B) (110 mg, 0.206 mmol) in TFA (2.0 mL, 26.0 mmol) and CH$_2$Cl$_2$ (2 mL) was stirred at RT for 1 h. The solvent was removed and the residue was dried in the vacuum to give the crude 4-(3-(5-chloro-2-(1H-tetrazol-1-yl)phenyl)-7-hydroxy-6,7-dihydro-5H-cyclopenta[b]pyridine-7-carboxamido)benzoic acid (19-C) which was used in the next step without further purification. LCMS: m/z 477.13 [M+H]$^+$.

Step 3: 4-[({3-[5-Chloro-2-(1H-tetrazol-1-yl)phenyl]-7-hydroxy-1-oxido-6,7-dihydro-5H-cyclopenta[b]-pyridine-7-yl}carbonyl)amino]benzoic acid (Example 19)

A solution of 4-(3-(5-chloro-2-(1H-tetrazol-1-yl)phenyl)-7-hydroxy-6,7-dihydro-5H-cyclopenta[b]pyridine-7-carboxamido)benzoic acid (19-C) (95 mg, 0.2 mmol) and peracetic acid (0.166 mL, 1.000 mmol) in acetic acid (2 mL) was stirred at RT overnight. The solvent was removed and the residue was purified by preparative reverse phase HPLC (C-18), eluting with Acetonitrile/Water+0.1% TFA, to give the title compound. LCMS: m/z 493.20 [M+H]$^+$.

Example 20

3-(5-Chloro-2-(H-tetrazol-1-yl)phenyl)-7-(4-((methoxycarbonyl)amino)benzamido)-6,7-dihydro-5H-cyclopenta[b]pyridine 1-oxide

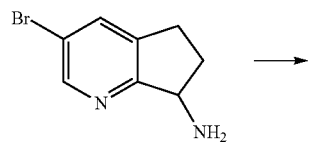

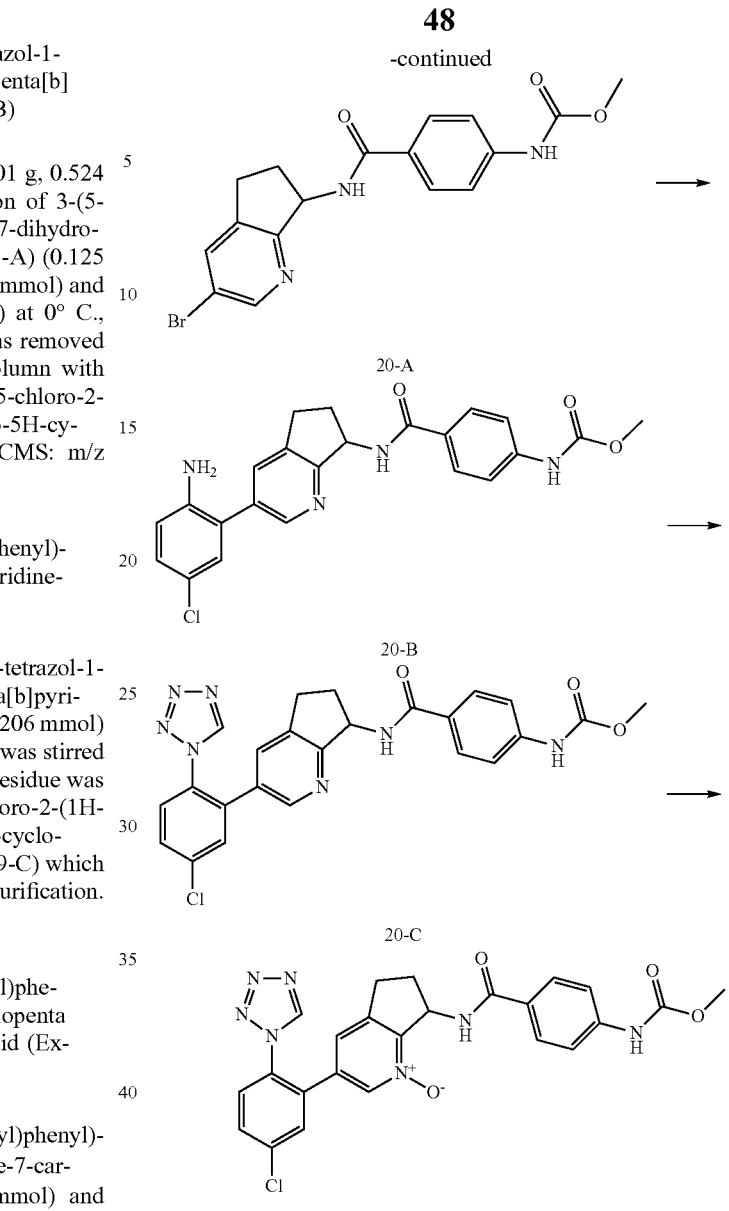

Example 20

Step 1: Methyl (4-((3-bromo-6,7-dihydro-5H-cyclopenta[b]pyridin-7-yl)carbamoyl)phenyl)-carbamate (20-A)

3-Bromo-6,7-dihydro-5H-cyclopenta[b]pyridin-7-amine (121 mg, 0.568 mmol), 4-((methoxycarbonyl)amino)benzoic acid (133 mg, 0.681 mmol), and HATU (324 mg, 0.852 mmol) were suspended in DMF (5 ml) and DIEA (0.298 ml, 1.704 mmol) was added. The resultant mixture was stirred at rt for 18 h. The reaction mixture was diluted with EtOAc, washed with satd. aq. LiCl, water and brine. The organic layer was dried over MgSO$_4$, filtered, and concentrated in vacuo. The residue was suspended in DCM, and the solid precipitate was isolated by filtration to give the title compound (20-A). The DCM filtrate was further purified by flash chromatography on silica gel (gradient elution; 0%-50% EtOAc/hexanes as eluent) to provide an additional quantity of the title compound (20-A). MS (ESI) m/z=390 [M+H].

Step 2: Methyl (4-((3-(2-amino-5-chlorophenyl)-6, 7-dihydro-5H-cyclopenta[b]pyridin-7-yl)carbamoyl) phenyl)carbamate (20-B)

Methyl (4-((3-bromo-6,7-dihydro-5H-cyclopenta[b]pyridin-7-yl)carbamoyl)phenyl)carbamate (155 mg, 0.397 mmol), 2-amino-5-chlorophenylboronic acid, pinacol ester (111 mg, 0.437 mmol), 1,1'-bis(diphenylphosphino)ferrocene-palladium(II)dichloride dichloromethane complex (58 mg, 0.079 mmol), and cesium fluoride (181 mg, 1.192 mmol) were suspended in 1,4-dioxane (7 mL) in a 20 mL microwave tube. The vial was crimped, and the reaction mixture was sparged with $N_2$, followed by heating in an oil bath at 110° C. for 1 h. The mixture was cooled to rt, diluted with EtOAc, and the resulting mixture was washed with water and brine. The layers were separated, and the organics were dried over $MgSO_4$, filtered, and concentrated in vacuo. The residue was purified by flash chromatography on silica gel (gradient elution; 0%-50% EtOAc/hexanes as eluent) to provide the title compound (20-B). MS (ESI) m/z=437 [M+H].

Step 3: Methyl (4-((3-(5-chloro-2-(1H-tetrazol-1-yl) phenyl)-6,7-dihydro-5H-cyclopenta-[b]pyridine-7-yl)carbamoyl)phenyl)carbamate Methyl (4-((3-(5-chloro-2-(1H-tetrazol-1-yl)phenyl)-6,7-dihydro-5H-cyclopenta[b]pyridin-7-yl)carbamoyl)phenyl)carbamate (62 mg, 0.142 mmol), sodium azide (46 mg, 0.710 mmol), and trimethyl orthoformate (78 µL, 0.710 mmol) were suspended in acetic acid (3 mL), and the mixture stirred at rt for 18 h. The reaction mixture was partitioned between EtOAc and water, the layers were separated. The organics were washed with brine, dried over $MgSO_4$, filtered, and concentrated in vacuo, co-evaporating w/toluene. The crude residue was purified by flash chromatography on silica gel (step gradient elution; 2.2%-5% MeOH/DCM as eluent) to provide the title compound (20-C). MS (ESI) m/z=490 [M+H].

Step 4: 3-(5-Chloro-2-(1H-tetrazol-1-yl)phenyl)-7-(4-((methoxycarbonyl)amino)benzamido)-6,7-dihydro-5H-cyclopenta[b]pyridine 1-oxide (Example 20)

Example 20 was prepared following procedures described previously in Example 1, Step 6 for the preparation of compound 1-I, substituting compound 20-C for compound 1-H. MS (ESI) m/z=506 [M+H].

Examples 21 and 22

7-((4-carboxyphenyl)carbamoyl)-3-(5-chloro-2-(1H-tetrazol-1-yl)phenyl)-7-(cyclopropylmethyl)-6,7-dihydro-5H-cyclopenta[b]pyridine 1-oxide (Example 21 and 22)

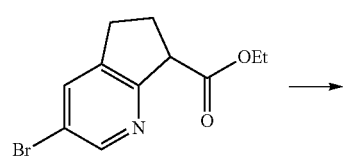

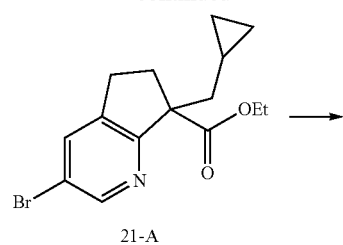

21-A

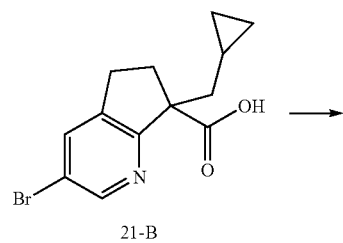

21-B

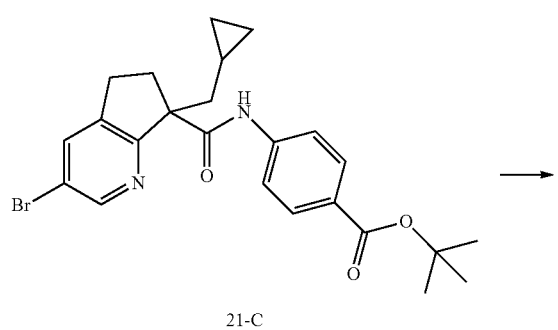

21-C

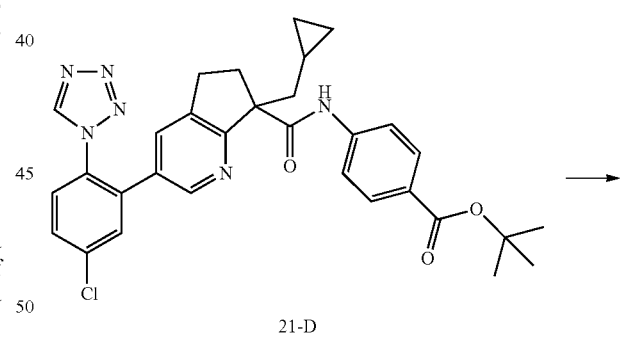

21-D

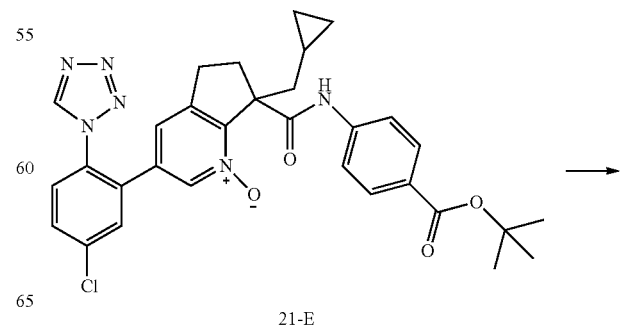

21-E

-continued

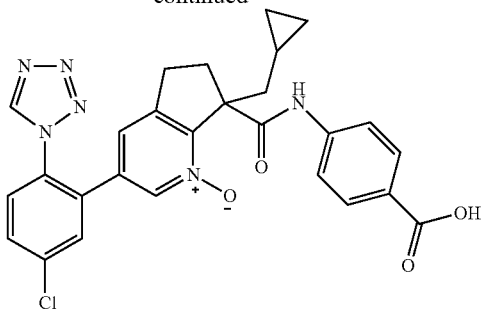

Compound 21 (enantiomer 1)
Compound 22 (enantiomer 2)

Step 1: Ethyl 3-bromo-7-(cyclopropylmethyl)-6,7-dihydro-5H-cyclopenta[b]pyridine-7-carboxylate (21-A)

Ethyl 3-bromo-6,7-dihydro-5H-cyclopenta[b]pyridine-7-carboxylate (2.5 g, 9.3 mmol) was dissolved in THF (30 ml), and cooled to −78° C. Lithium bis(trimethylsilyl)amide (11 ml, 11 mmol) was added. The mixture was stirred for 1.5 hours. (Iodomethyl)cyclopropane (1.2 ml, 13 mmol) was added slowly. The mixture was stirred at −78° C. for one hour, then at room temperature overnight. The reaction was quenched with the addition of saturated aqueous $NH_4Cl$ solution (7 mL). The product was extracted with ethyl acetate, and washed with brine. The organic layer was dried over anhydrous sodium sulfate. After it was filtered and concentrated, the crude was purified by column chromatography on 80 g prepacked silica gel column, eluting with gradient 0-30% EtOAc/isohexane to give the product (21-A). MS (ESI) m/z=325.9 [M+H].

Step 2: 3-Bromo-7-(cyclopropylmethyl)-6,7-dihydro-5H-cyclopenta[b]pyridine-7-carboxylic acid lithium salt (21-B)

Ethyl 3-bromo-7-(cyclopropylmethyl)-6,7-dihydro-5H-cyclopenta[b]pyridine-7-carboxylate (21-A, 1.5 g, 4.63 mmol) in MeOH (15 ml) was mixed with LiOH (6.94 ml, 6.94 mmol) and heated to 50° C. for 30 minutes. The mixture was concentrated to dryness, then further dried in a vacuum oven at 50° C. for 3 days. The product was used directly in the next step without further treatment. MS (ESI) m/z=297.8 [M+H].

Step 3: tert-Butyl 4-(3-bromo-7-(cyclopropylmethyl)-6,7-dihydro-5H-cyclopenta[b]pyridine-7-carboxamido)benzoate. (21-C)

Lithium 3-bromo-7-(cyclopropylmethyl)-6,7-dihydro-5H-cyclopenta[b]pyridine-7-carboxylate (21-B, 0.3 g, 1 mmol) in DMF (1.50 ml) was mixed with HATU (0.45 g, 1.2 mmol). The mixture was heated to 45° C. tert-Butyl 4-aminobenzoate (0.23 g, 1.2 mmol) was added, then the mixture was heated at 45° C. overnight. After it cooled to room temperature, the mixture was poured into 40 mL of water while stirring. The product was extracted with ethyl acetate. The organic layer was separated, and washed with brine. After it was dried over anhydrous sodium sulfate, the solution was concentrated. The crude was purified by column chromatography on a 50 g prepacked silica gel column, eluting with gradient 0-60% EtOAc/isohexane to give the product. (21-C). MS (ESI) m/z=472.9 [M+H].

Step 4: tert-Butyl 4-(3-(5-chloro-2-(1H-tetrazol-1-yl)phenyl)-7-(cyclopropylmethyl)-6,7-dihydro-5H-cyclopenta[b]pyridine-7-carboxamido)benzoate (21-D)

tert-Butyl 4-(3-bromo-7-(cyclopropylmethyl)-6,7-dihydro-5H-cyclopenta[b]pyridine-7-carboxamido)benzoate (550 mg, 1.17 mmol) was mixed with 4,4,4',4',5,5,5',5'-octamethyl-2,2'-bi(1,3,2-dioxaborolane) (300 mg, 1.17 mmol), [1,1'-bis(diphenylphosphino)ferrocene]dichloropalladium(II) (171 mg, 0.23 mmol), and potassium acetate (340 mg, 3.5 mmol) in a microwave reaction vial. The vial was then capped. Air was removed by vacuum, and it was back-filled with nitrogen (×3). 1,4-Dioxane (5.5 ml) was introduced by syringe. The mixture was then heated to 110° C. for 45 minutes. After it was cooled to room temperature, 1-(4-chloro-2-iodophenyl)-1H-tetrazole (0.358 g, 1.167 mmol) and [1,1'-bis(diphenylphosphino)ferrocene]dichloropalladium (II) (0.085 g, 0.117 mmol) were added. The reaction vial was capped. Air was removed by vacuum, and it was back-filled with nitrogen (×3). A solution of $K_2CO_3$ (1M, 3.50 ml, 3.50 mmol) was introduced with a syringe. The mixture was then heated to 80° C. for 2 hours. The mixture was diluted with ethyl acetate, and filtered. The organic layer was separated. After it was dried over anhydrous sodium sulfate, the solution was concentrated. The crude was purified by column chromatography on a 100 g prepacked silica gel column, eluting with gradient 10~100% EtOAc/isohexane to give the product. (21-D). MS (ESI) m: =571.1 [M+H].

Step 5: 7-((4-(tert-Butoxycarbonyl)phenyl)carbamoyl-3-(5-chloro-2-(1H-tetrazol-1-yl)phenyl)-7-(cyclopropylmethyl-6,7-dihydro-5H-cyclopenta[b]pyridine 1-oxide (21-E)

tert-Butyl 4-(3-(5-chloro-2-(1H-tetrazol-1-yl)phenyl)-7-(cyclopropylmethyl)-6,7-dihydro-5H-cyclopenta[b]pyridine-7-carboxamido)benzoate (300 mg, 0.53 mmol) in DCM (3 ml) was mixed with mCPBA (168 mg, 0.68 mmol), then stirred at room temperature for 15 hours. The mixture was concentrated, and purified by column chromatography on a 100 g prepacked silica gel column, eluting with 0~80% gradient EtOAc/isohexane to give the product (21-E). MS (ESI) m/z=587.1 [M+H].

Step 6: 7-((4-carboxyphenyl)carbamoyl)-3-(5-chloro-2-(H-tetrazol-1-yl)phenyl)-7-(cyclopropylmethyl)-6,7-dihydro-5H-cyclopenta[b]pyridine 1-oxide (Example 21 and 22)

7-((4-(tert-Butoxycarbonyl)phenyl)carbamoyl)-3-(5-chloro-2-(1H-tetrazol-1-yl)phenyl)-7-(cyclopropylmethyl)-6,7-dihydro-5H-cyclopenta[b]pyridine 1-oxide (21-E, 290 mg, 0.49 mmol) in DCM (2 ml) was mixed with TFA (2.0 ml), then stirred at room temperature for 2 hours. Toluene (15 mL) was added. The mixture was concentrated by a rotavapor. The crude was purified by column chromatography on a 50 g prepacked silica gel column, eluting with 0~8% gradient $CH_2Cl_2$/MeOH to give the product. The racemic product was separated by chiral SFC chromatography on an IA column, eluting with 70% 2:1 MeOH:MeCN/$CO_2$ to give the two enantiomers. Example 21 is the fast eluting enantiomer, MS (ESI) m/z=530.8 [M+H], and Example 22 is the slow eluting enantiomer, MS (ESI) m/z=530.8 [M+H]

Factor XIa Assay

The effectiveness of a compound of the present invention as an inhibitor of Coagulation Factor XIa can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 150 mM NaCl, 5 mM $CaCl_2$, and 0.1% PEG 8000 (polyethylene glycol; JT Baker or Fisher Scientific). Determinations were made using purified human Factor XIa at a final concentration of 40 pM (Sekisui Diagnostics) and the synthetic substrate, Z-Gly-Pro-Arg-AFC, TFA salt (Sigma #C0980) at a concentration of 100 µM.

Activity assays were performed by diluting a stock solution of substrate at least tenfold to a final concentration ≤0.1 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m/[S]$, $[I]/e$, and $[I]/e$ (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in the following equation.

$$V_o/V_i = 1 + [I]/K_i$$

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

| Factor XIa inhibition | |
|---|---|
| Example | hFXIa IC50 (nM) |
| 1 | 3.8 |
| 2 | 1997 |
| 3 | 2918 |
| 4 | 2370 |
| 5 | 3.6 |

-continued

| Factor XIa inhibition | |
|---|---|
| Example | hFXIa IC50 (nM) |
| 6 | 10.5 |
| 7 | 8.6 |
| 8 | 4.2 |
| 9 | 2.9 |
| 10 | 2.7 |
| 11 | 103.8 |
| 12 | 202.2 |
| 13 | 3.7 |
| 14 | 219 |
| 15 | 14.1 |
| 16 | 85.6 |
| 17 | 4444 |
| 18 | 9451 |
| 19 | 6.0 |
| 20 | 893.6 |
| 21 | >870 |
| 22 | 178 |

Kallikrein Assay

The effectiveness of a compound of the present invention as an inhibitor of Kallikrein can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the inhibitory constant, $K_i$.

Kallikrein determinations were made in 50 mM HEPES buffer at pH 7.4 containing 150 mM NaCl, 5 mM $CaCl_2$, and 0.1% PEG 8000 (polyethylene glycol; Fisher Scientific). Determinations were made using purified Human plasma kallikrein at a final concentration of 0.5 nM (Enzyme Research Laboratories) and the synthetic substrate, Acetyl-K-P-R-AFC (Sigma # C6608) at a concentration of 100 mM.

Activity assays were performed by diluting a stock solution of substrate at least tenfold to a final concentration ≤0.2 $K_m$ into a solution containing enzyme or enzyme equilibrated with inhibitor. Times required to achieve equilibration between enzyme and inhibitor were determined in control experiments. The reactions were performed under linear progress curve conditions and fluorescence increase measured at 405 Ex/510 Em nm. Values were converted to percent inhibition of the control reaction (after subtracting 100% Inhibition value). $IC_{50}$ was determined by inflection point from a four parameter logistic curve fit. Ki was calculated using the Cheng Prusoff equation, $Ki=IC_{50}/(1+([S]/Km))$.

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

| Kalikrein inhibition | |
|---|---|
| Examples | hFXIa IC50 (nM) |
| 1 | 472.7 |
| 5 | 504.0 |
| 6 | 699.9 |
| 7 | 1715.0 |
| 8 | 815.9 |
| 9 | 460.3 |
| 10 | 529.7 |
| 13 | 201.8 |
| 15 | 4917 |
| 19 | 1369 |

What is claimed is:

1. A compound of the formula:

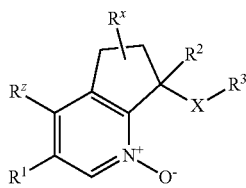

wherein X is (C=O)NH or —NH(C=O)—;

$R^1$ is aryl, heteroaryl or $C_{3-6}$ cycloalkyl, wherein said aryl, heteroaryl and cycloalkyl groups are optionally substituted with one to three substituents independently selected from the group consisting of halo, nitro, cyano, oxo, $R^4$, $OR^4$, (C=O)$R^4$, (C=O)$OR^4$, $NR^4R^5$, NH(C=O)$R^4$, NH(C=O)$OR^4$, $C_{3-6}$ cycloalkyl and heteroaryl which is optionally substituted with $R^4$;

$R^2$ is hydrogen, hydroxy, halo or $C_{1-6}$ alkyl, wherein said alkyl is optionally substituted with one or two substituents independently selected from the group consisting of halo, $OR^4$ or $C_{3-6}$ cycloalkyl;

$R^3$ is aryl, heteroaryl or $C_{3-10}$ cycloalkyl wherein said aryl, heteroaryl and cycloalkyl groups are optionally substituted with one to three substituents independently selected from the group consisting of halo, nitro, cyano, oxo, $R^4$, $OR^4$, (C=O)$R^4$, (C=O)$OR^4$, $NR^4R^5$, NH(C=O)$R^4$, NH(C=O)$OR^4$ and heteroaryl;

$R^4$ is hydrogen or $C_{1-6}$ alkyl, which is optionally substituted with one to three groups independently selected from the group consisting of halo and hydroxy;

$R^5$ is hydrogen or $C_{1-6}$ alkyl, which is optionally substituted with one to three groups independently selected from the group consisting of halo and hydroxy;

$R^x$ is hydrogen, hydroxy or halo;

$R^z$ is hydrogen, hydroxy, methoxy or halo;

or a pharmaceutically acceptable salt thereof.

2. The compound of claim 1 of the formula:

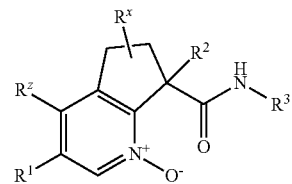

wherein $R^1$ is phenyl, which is optionally substituted with one to three substituents independently selected from the group consisting of halo or heteroaryl which is optionally substituted with $R^4$;

$R^2$ is hydrogen, hydroxy, halo, or $C_{1-6}$ alkyl, wherein said alkyl is optionally substituted with one or two substituents independently selected from the group consisting of halo, $OR^4$ or $C_{3-6}$ cycloakyl;

$R^3$ is phenyl or $C_{3-10}$ cycloalkyl, wherein said phenyl and cycloalkyl groups are optionally substituted with one to three substituents independently selected from the group consisting of halo, cyano, oxo, $R^4$, $OR^4$, (C=O)$R^4$, (C=O)$OR^4$ and NH(C=O)$R^4$;

$R^4$ is hydrogen, or $C_{1-6}$ alkyl, which is optionally substituted with one to three groups of independently selected from the group consisting of halo and hydroxy;

$R^5$ is hydrogen or $C_{1-6}$ alkyl, which is optionally substituted with one to three groups independently selected from the group consisting of halo and hydroxy;

$R^x$ is hydrogen, hydroxy or halo;

$R^z$ is hydrogen, hydroxy, methoxy or halo;

or a pharmaceutically acceptable salt thereof.

3. The compound of claim 1 wherein $R^1$ is phenyl, which optionally is substituted with two or three substituents independently selected from the group consisting of halo and heteroaryl; or a pharmaceutically acceptable salt thereof.

4. The compound of claim 1 wherein $R^1$ is phenyl, which optionally is substituted with halo and tetrazolyl; or a pharmaceutically acceptable salt thereof.

5. The compound of claim 1 where in $R^1$ is phenyl, which optionally is substituted with three halo; or a pharmaceutically acceptable salt thereof.

6. The compound of claim 1 wherein $R^2$ is hydroxy; or a pharmaceutically acceptable salt thereof.

7. The compound of claim 1 wherein $R^3$ is phenyl, which is optionally substituted with one to three substituents independently selected from the group consisting of (C=O)$OR^4$ and NH(C=O)$R^4$; or a pharmaceutically acceptable salt thereof.

8. The compound of claim 1 wherein $R^3$ is phenyl, which is substituted with (C=O)$OR^4$; or a pharmaceutically acceptable salt thereof.

9. The compound of claim 1 selected from:

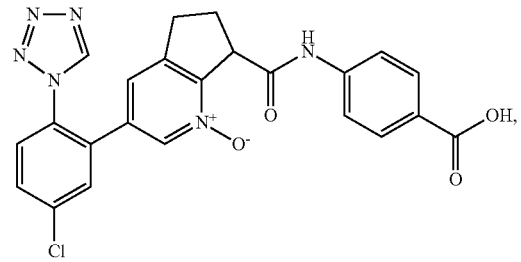

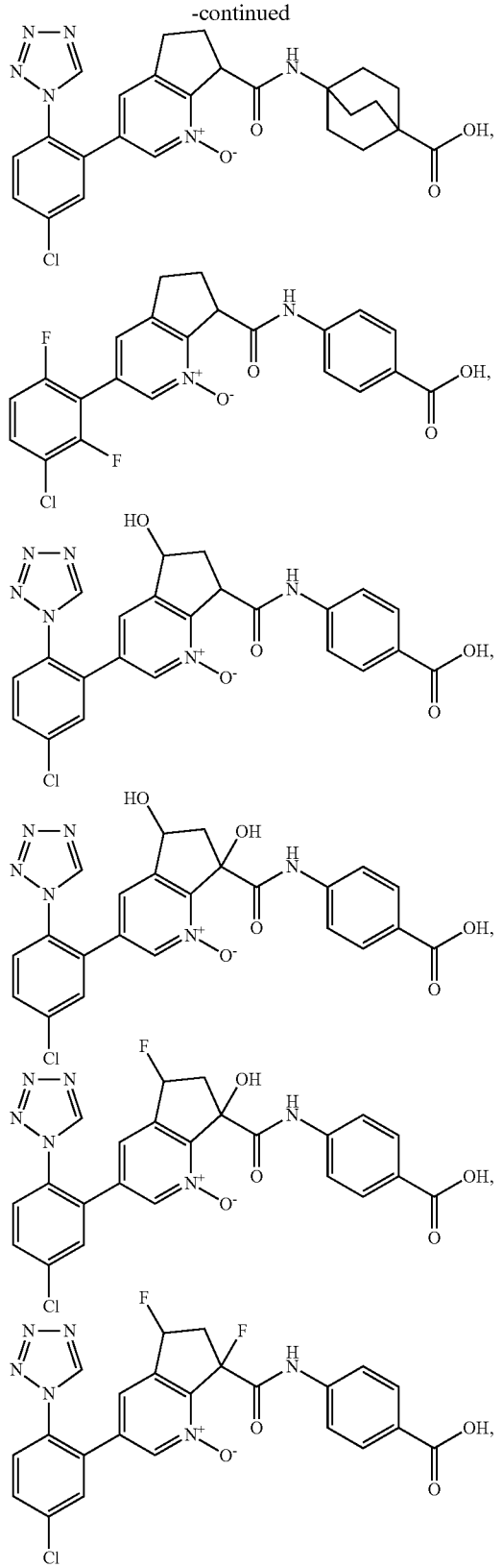

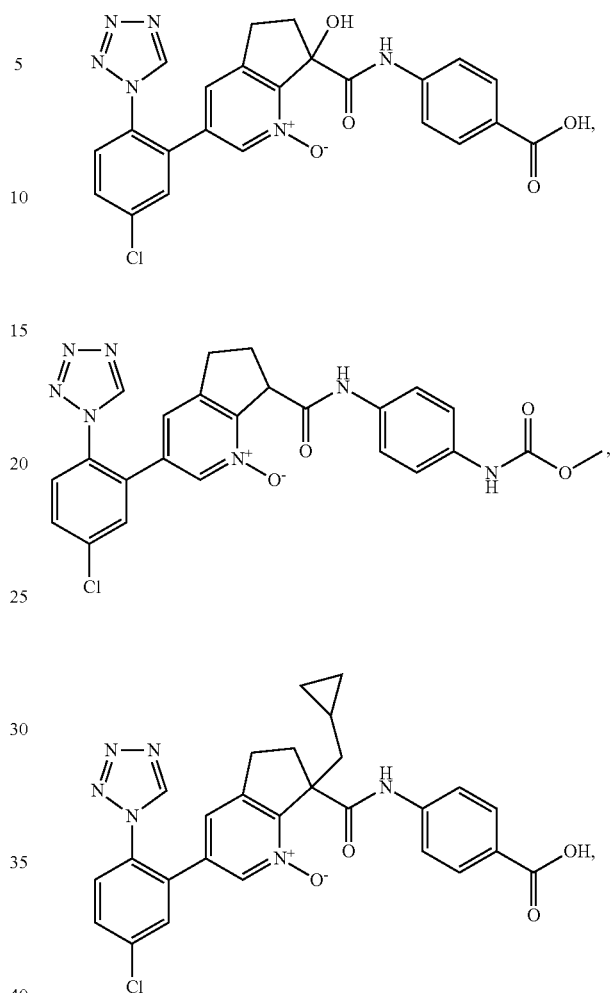

or a pharmaceutically acceptable salt thereof.

10. A pharmaceutical composition comprising a compound of claim 1 or a pharmaceutically acceptable salt thereof and a pharmaceutically acceptable carrier.

11. A method for inhibiting thrombus formation in blood or treating thrombus formation in blood comprising administering a composition of claim 10 to a mammal in need of thereof.

12. A method of treating venous thromboembolism and pulmonary embolism in a mammal comprising administering a composition of claim 10 to a mammal in need thereof.

13. A method of treating deep vein thrombosis in a mammal comprising administering a composition of claim 10 to a mammal in need thereof.

14. A method of treating thromboembolic stroke in a human comprising administering a composition of claim 10 to a mammal in need thereof.

* * * * *